United States Patent
Chang et al.

(10) Patent No.: US 8,758,412 B2
(45) Date of Patent: Jun. 24, 2014

(54) INTEGRATED IPD DEVICES, METHODS, AND SYSTEMS

(75) Inventors: Matthew Y. Chang, Yorktown, VA (US); Geoffrey J. Raicer, Phoenix, AZ (US); Bradford A. Donovan, Scottsdale, AZ (US)

(73) Assignee: Pachyderm Medical, L.L.C., Phoenix, AZ (US)

( * ) Notice: Subject to any disclaimer, the term of this patent is extended or adjusted under 35 U.S.C. 154(b) by 185 days.

(21) Appl. No.: 13/231,646

(22) Filed: Sep. 13, 2011

(65) Prior Publication Data

US 2012/0071925 A1  Mar. 22, 2012

Related U.S. Application Data

(60) Provisional application No. 61/384,311, filed on Sep. 20, 2010.

(51) Int. Cl.
*A61B 17/88* (2006.01)

(52) U.S. Cl.
USPC ............................ 606/279; 606/248; 606/249

(58) Field of Classification Search
USPC .................................. 606/248, 249, 279, 90
See application file for complete search history.

(56) References Cited

U.S. PATENT DOCUMENTS

| | | | |
|---|---|---|---|
| 5,255,691 | A | 10/1993 | Otten |
| 5,836,948 | A | 11/1998 | Zucherman et al. |
| 6,699,246 | B2 | 3/2004 | Zucherman et al. |
| 6,830,570 | B1 | 12/2004 | Frey et al. |
| 6,926,728 | B2 | 8/2005 | Zucherman et al. |
| 2002/0019637 | A1 | 2/2002 | Frey et al. |
| 2003/0216737 | A1 | 11/2003 | Biscup |
| 2005/0055031 | A1 | 3/2005 | Lim |
| 2005/0165398 | A1 | 7/2005 | Reiley |
| 2006/0036273 | A1 | 2/2006 | Siegal |
| 2006/0085070 | A1 | 4/2006 | Kim |

(Continued)

FOREIGN PATENT DOCUMENTS

| | | |
|---|---|---|
| WO | 2005-009300 | 2/2005 |
| WO | 2006-135889 | 12/2006 |

(Continued)

OTHER PUBLICATIONS

Bono, et al., "Interspinous process devices in the lumbar spine", J Spinal Disord Tech. 20(3):255-61, May 2007.

(Continued)

*Primary Examiner* — Eduardo C Robert
*Assistant Examiner* — Julianna N Harvey
(74) *Attorney, Agent, or Firm* — Bradford A. Donovan

(57) ABSTRACT

The present invention relates generally to various integrated Inter-Spinous Process Decompression, IPD, devices and methods for implantation thereof for treating spinal stenosis. Generally, in accordance with an exemplary embodiment of the present invention, the disclosed IPD system comprises an IPD tusk-shaped needle, an IPD tusk-shaped sizer, an IPD tusk-shaped implant tool, and an IPD implant.
Preferably, in accordance with an exemplary embodiment of the present invention, each of the IPD tusk-shaped needle, the IPD tusk-shaped sizer, the IPD tusk-shaped implant tool, and IPD implant are suitably configured for percutaneous insertion between a patient's spinous process. Most preferably, in accordance with an exemplary embodiment of the present invention, either the IPD tusk-shaped sizer or the IPD tusk-shaped implant tool is configured to be reversibly coupled to an IPD implant.

16 Claims, 12 Drawing Sheets

(56) References Cited

U.S. PATENT DOCUMENTS

| | | |
|---|---|---|
| 2006/0089654 A1 | 4/2006 | Lins et al. |
| 2006/0149278 A1 | 7/2006 | Abdou |
| 2006/0184248 A1 | 8/2006 | Edidin et al. |
| 2006/0195102 A1 | 8/2006 | Malandain |
| 2006/0241648 A1 | 10/2006 | Bleich et al. |
| 2007/0149972 A1 | 6/2007 | Nakajima et al. |
| 2007/0213734 A1 | 9/2007 | Bleich et al. |
| 2008/0027438 A1 | 1/2008 | Abdou |
| 2008/0033552 A1 | 2/2008 | Lee et al. |
| 2008/0082172 A1 | 4/2008 | Jackson |
| 2008/0086034 A1 | 4/2008 | Schmitz et al. |
| 2008/0086114 A1 | 4/2008 | Schmitz et al. |
| 2008/0091227 A1 | 4/2008 | Schmitz et al. |
| 2008/0091269 A1 | 4/2008 | Zipnick et al. |
| 2008/0103504 A1 | 5/2008 | Schmitz et al. |
| 2008/0108990 A1 | 5/2008 | Mitchell et al. |
| 2008/0119846 A1* | 5/2008 | Rioux ............... 606/41 |
| 2008/0161822 A1 | 7/2008 | Perez-Cruet et al. |
| 2008/0167657 A1 | 7/2008 | Greenhalgh |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0229597 A1 | 9/2008 | Malandain |
| 2008/0243250 A1* | 10/2008 | Seifert et al. ........ 623/17.16 |
| 2008/0275458 A1 | 11/2008 | Bleich et al. |
| 2008/0312660 A1 | 12/2008 | Bleich et al. |
| 2009/0018507 A1 | 1/2009 | Schmitz et al. |
| 2009/0024203 A1 | 1/2009 | Hestad et al. |
| 2009/0099603 A1 | 4/2009 | Nishida |
| 2009/0138056 A1 | 5/2009 | Anderson et al. |
| 2009/0143829 A1 | 6/2009 | Shluzas |
| 2010/0004654 A1* | 1/2010 | Schmitz et al. ........ 606/90 |

FOREIGN PATENT DOCUMENTS

| | | |
|---|---|---|
| WO | 2007-018114 | 2/2007 |
| WO | 2007-079237 | 7/2007 |
| WO | 2007-117882 | 10/2007 |
| WO | 2008-068162 | 6/2008 |

OTHER PUBLICATIONS

Chiu, "Treatment of Lumbar Spinal Stenosis With Interspinous Process Decompression System (IPD) (X-Stop®)", The Internet Journal of Minimally Invasive Spinal Technology. 2007. vol. 1 No. 1.

Khoo, et al., "Minimally Invasive Percutaneous Posterior Lumbar Interbody Fusion", Neurosurgery, 51[Suppl 2]: S2-166-S2-181, Nov. 2002.

Kim, et al., "Interspinous process spacers", J Am Acad Orthop Surg. 15(4):200-7, Apr. 2007.

Kim, et al., "Dynamic intraspinous spacer technology for posterior stabilization: case-control study on the safety, sagittal angulation, and pain outcome at 1-year follow-up evaluation", Neurosurg Focus, 22(1):E7, 2007.

Podichetty, et al., "Complications Associated With Minimally Invasive Decompression for Lumbar Spinal Stenosis", J Spinal Disord Tech. 19(3):161-166, May 2006.

Poelstra, et al., "Minimally invasive exposure techniques in spine surgery", Current Opinion in Orthopedics. 17 (3):208-213, Jun. 2006.

Shiraishi, "A new technique for exposure of the cervical spine laminae Technical note", J Neurosurg. (Spine 1) 96:122-126, 2002.

Singh, et al., "Lumbar Spinal Stenosis", J Am Acad Orthop Surg. 16(3):171-176, Mar. 2008.

Wilke, et al., "Biomechanical effect of different lumbar interspinous implants on flexibility and intradiscal pressure", Eur Spine J. 17(8):1049-56, Jun. 2008.

Yano, et al. "A new ceramic interspinous process spacer for lumbar spinal canal stenosis", Neurosurgery. 63[ONS Suppl 1]:ONS108-13; discussion ONS114, Jul. 2008.

* cited by examiner

INTEGRATED IPD DEVICES, METHODS, AND SYSTEMS

CROSS-REFERENCE TO RELATED APPLICATIONS

This application claims the benefit of U.S. Provisional Application No. 61/384,311 filed on Sep. 20, 2010, the contents of which is hereby incorporated by reference in its entirety.

FIELD OF INVENTION

The present invention relates generally to various integrated Inter-Spinous Process Decompression, IPD, devices and methods for implantation thereof for treating spinal stenosis. Generally, in accordance with an exemplary embodiment of the present invention, the disclosed IPD system comprises an IPD tusk-shaped needle, an IPD tusk-shaped sizer, an IPD tusk-shaped implant tool, and an IPD implant.

Preferably, in accordance with an exemplary embodiment of the present invention, each of the IPD tusk-shaped needle, the IPD tusk-shaped sizer, the IPD tusk-shaped implant tool, and IPD implant are suitably configured for percutaneous insertion between a patient's spinous process. Most preferably, in accordance with an exemplary embodiment of the present invention, either the IPD tusk-shaped sizer or the IPD tusk-shaped implant tool is configured to be reversibly coupled to an IPD implant.

BACKGROUND OF THE INVENTION

Spinal stenosis is a medical condition in which the spinal canal narrows and compresses the spinal cord and nerves. This is usually due to the natural process of spinal degeneration that occurs with aging. It can also sometimes be caused by spinal disc herniation, osteoporosis or a tumor. Spinal canal is a column, and loss of height equals loss of volume. As a result, canal becomes tight and narrowed.

Spinal stenosis typically affects the lumbar vertebrae, the largest segments of the movable part of the vertebral column, characterized by the absence of the foramen transversarium within the transverse process, and by the absence of facets on the sides of the body (the lumbar vertebrae are designated L1 to L5, starting at the top). Lumbar spinal stenosis may result in Neurogenic claudication causing pain and/or weakness in the legs, buttocks, or thighs, and/or feet. Neurogenic claudication may also result in loss of bladder and/or bowel control.

The pathophysiology of Neurogenic claudication is thought to be ischemia of the lumbosacral nerve roots secondary to compression from surrounding structures, hypertrophied facets, ligamentum flavum, bone spurs, scar tissue, and bulging or herniated discs. Typically, pain occurs with standing because as you axially load the spine it compresses losing height (and volume) and pinches nerves. Commonly, there is little or no pain when sitting because the spine is unloaded and flexed increasing length (and volume) making more room for nerves.

Currently, patients suffering from severe spinal stenosis have few surgical options to alleviate symptoms including a Laminectomy, a Foraminotomy, and surgical placement of an implant device within the spinous processes. One option is a Laminectomy wherein a portion of the vertebral bone called the lamina is surgically removed. There are many variations of Laminectomy, in the most minimal form small skin incisions are made, back muscles are pushed aside rather than cut, and the parts of the vertebra adjacent to the lamina are left intact. The traditional form of Laminectomy (conventional Laminectomy) excises much more than just the lamina, the entire posterior backbone is removed, along with overlying ligaments and muscles. The usual recovery period is very different depending on which type of Laminectomy has been performed: days in the minimal procedure, and weeks to months with conventional open surgery.

Conventional open Laminectomy often involves excision of the posterior spinal ligament, and some or all of the spinous process, and facet joint. Removal of these structures, in the open technique, requires cutting the many muscles of the back which attach to them. Laminectomy performed as a minimal spinal surgery procedure, however, allows the bellies of muscles to be pushed aside instead of transected, and generally involves less bone removal than the open procedure. The actual bone removal may be carried out with a variety of surgical tools, including drills, rongeurs, and lasers.

Removal of substantial amounts of bone and tissue may require additional procedures to stabilize the spine, such as fusion procedures, and spinal fusion generally requires a much longer recovery period than simple Laminectomy.

In hopes of finding a less invasive procedure to alleviate pain caused by spinal stenosis, physicians have turned to Inter-Spinous Process Decompression, IPD, in which an implant is placed/implanted between the spinous processes of the symptomatic disc levels. These devices are designed to limit pathologic extension of the spinal segments and maintain them in a neutral or slightly flexed position, which may allow patients to resume their normal posture rather than flex the entire spine to gain symptom relief.

Unfortunately, implantation of many of these IPD devices still results in significant trauma to the patient, requiring open incisions and retraction of muscle and tissue. For example, the X-Stop implant, developed by Saint Francis Medical Technologies, L.L.C. covered by a litany of patent applications and issued United States patents (e.g. U.S. Pat. No. 5,836,948), herein incorporated by reference, requires that the physician make an invasive incision and wedge the implant between the spinous process to push them apart (permanently increasing the spinal column volume).

Thus, integrated IPD devices, methods, and systems allowing for a minimally invasive, percutaneous implantation are needed and are provided herein.

SUMMARY OF THE INVENTION

Seventy-six million American children were born between 1946 and 1964. This group of people is affectionately known as the "Baby Boomers." Over the next few decades, healthcare issues associated with this large group of aging Baby Boomers will require innovation and simplified, minimally invasive medical solutions. It is anticipated that there will be an increase in adverse spinal conditions, which are characteristic of older people. Particularly, as discussed above, spinal stenosis (including but not limited to central canal and lateral stenosis) will become a major healthcare issue for many Americans and others globally. Accordingly, integrated Inter-Spinous Process Decompression, IPD, devices, methods, and systems allowing for a minimally invasive, percutaneous implantation are needed and are provided herein.

The present invention relates generally to various integrated Inter-Spinous Process Decompression, IPD, devices, methods, and systems treatment of spinal stenosis in a minimally invasive manner through precutaneous stab incisions. Preferably, in accordance with an exemplary embodiment of the present invention, the IPD tusk-shaped needle is coupled to a guide wire and percutaneously inserted in a patient's back via a stab incision. The IPD tusk-shaped needle is pushed (moved or inserted) between the patient's spinous process and exits the patient's back through an exit puncture wound. In accordance with an exemplary embodiment of the present invention, the IPD tusk-shaped needle is configured to stick out of both the stab incision entrance wound and the exit puncture wound simultaneously.

Secondly, in accordance with an exemplary embodiment of the present invention, the IPD tusk-shaped needle is removed and the guide wire is left in place. The guide wire will provide a guide for both the IPD tusk-shaped sizer and the IPD tusk-shaped implant tool.

Once the IPD tusk-shaped needle is removed and the guide wire is in place, the IPD tusk-shaped sizer is placed around the guide wire (guide wire is passed through the IPD tusk-shaped sizer) and pushed (moved or inserted) between the patient's spinous process until the spinous process is sufficiently dilated and the IPD implant sizer is used to determine the correct-sized implant for the patient. Preferably, in accordance with an exemplary embodiment of the present invention, the IPD tusk-shaped sizer comprises a curved dilator suitable for percutaneous insertion between and sizing of a patient's spinous process. In accordance with an exemplary embodiment of the present invention, the IPD tusk-shaped sizer is configured to stick out of both the stab incision entrance wound and the exit puncture wound simultaneously.

Most preferably, in accordance with an exemplary embodiment of the present invention, the dilator portion of the IPD tusk-shaped sizer comprises a measurement region, which gradually increases and is labeled for imaging.

Once the patient's implant size is determined, the IPD tusk-shaped sizer is either partially or fully removed. In one exemplary embodiment of the present invention, the measurement region of the IPD tusk-shaped sizer comprises detachably coupled measurement regions. In this exemplary embodiment, the IPD tusk-shaped size is partially removed and all measurement regions greater in diameter than the determined implant size for the patient are removed and replaced with an IPD implant detachably coupled to the IPD tusk-shaped sizer.

In an alternative exemplary embodiment of the present invention, the IPD tusk-shaped sizer is completely removed from the patient's back and the guide wire and an IPD tusk-shaped implant tool is placed around the guide wire (guide wire is passed through the IPD tusk-shaped implant tool). In this exemplary embodiment, the IPD tusk-shaped implant tool comprises an insertion portion suitable for dilating a patient's spinous process in preparation for fitting the spinous process with an implant, a dilator portion extending from the insertion portion, and an IPD implant detachably coupled at the end of said dilator portion. Preferably, in accordance with an exemplary embodiment of the present invention, the IPD tusk-shaped s implant tool is configured to stick out of both the stab incision entrance wound and the exit puncture wound simultaneously.

In accordance with this exemplary embodiment, the IPD tusk-shaped implant tool is pushed (moved or inserted) between a patient's spinous process, wherein the dilator portion dilates the patient's spinous process until the detachable IPD implant is securely positioned within the spinous process. Once the insertion portion of the IPD implant tool exits the exit puncture wound, the IPD implant tool is then pulled to securely place/implant the IPD implant in the patient's spinous process.

Once, the IPD implant is securely placed/implanted in the patient's spinous process, the IPD implant is detached from the IPD tusk-shaped implant tool, the IPD tusk-shaped implant tool (without the IPD implant) is removed from the patient's back, and the IPD implant is positioned between the patient's spinous process.

BRIEF DESCRIPTION OF THE DRAWING

A more complete understanding of the present invention, however, may best be obtained by referring to the detailed description when considered in connection with the drawing figures, wherein like numerals denote like elements and wherein.

DETAILED DESCRIPTION OF EXEMPLARY EMBODIMENTS

The detailed description of exemplary embodiments of the invention herein, shows various exemplary embodiments and the best modes, known to the inventors at this time. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those of reasonable skill in the art. Additionally, all included figures are non-limiting illustrations of the exemplary embodiments and modes, which similarly avail themselves to any equivalent modes or embodiments that are known or obvious to those of reasonable skill in the art.

The present invention relates generally to various integrated Inter-Spinous Process Decompression, IPD, devices, methods, and systems treatment of spinal stenosis in a minimally invasive manner through precutaneous stab incisions and preferably on an outpatient basis. Generally, in accordance with an exemplary embodiment of the present invention, the disclosed IPD system comprises an IPD tusk-shaped needle, an IPD tusk-shaped sizer, an IPD tusk-shaped implant tool, and IPD implant.

Preferably, in accordance with an exemplary embodiment of the present invention, each of the IPD tusk-shaped needle, the IPD tusk-shaped sizer, the IPD tusk-shaped implant tool, and the IPD implant are suitably configured for percutaneous insertion between a patient's spinous process. Most preferably, in accordance with an exemplary embodiment of the present invention, either the IPD tusk-shaped sizer or the IPD tusk-shaped implant tool is configured to be reversibly coupled to an IPD implant.

Inter-Spinous Process Decompression (IPD) Tusk-Shaped Needle Device and Method

Figure 1:
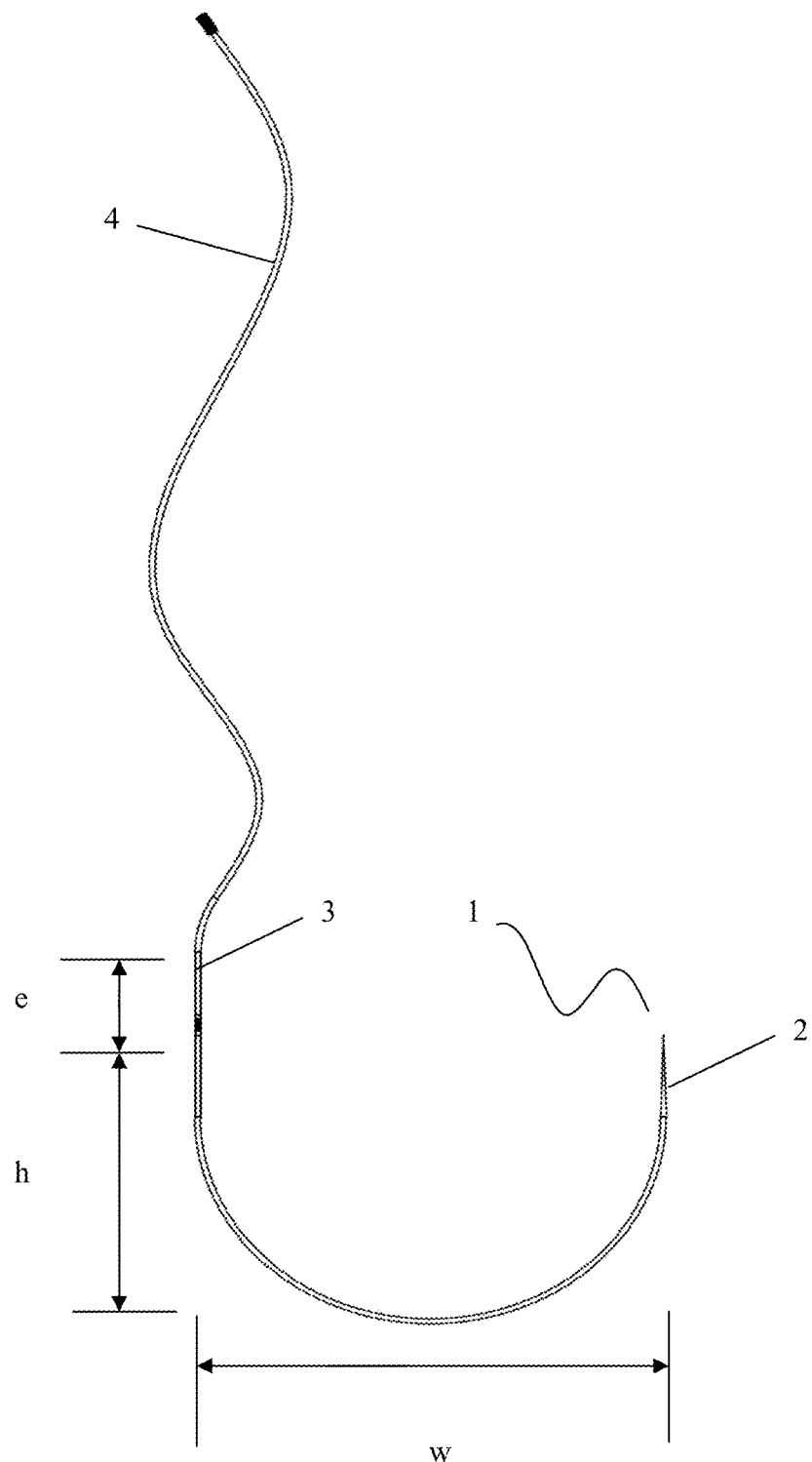
FIG. 1 illustrates an IPD tusk-shaped needle in accordance with one exemplary embodiment of the present invention.

As illustrated in FIG. 1 and in accordance with an exemplary embodiment of the present invention, the IPD tusk-shaped needle 1 comprises a curved, rigid (solid) body with an insertion end 2 at one end of the body suitable for percutaneous insertion into a patient's back and a trailing end 3 at the opposite end of the body suitable for coupling to a guide wire 4. Preferably, in accordance with an exemplary embodiment of the present invention, the IPD tusk-shaped needle 1 may comprise any material suitable for insertion between a patient's spinous process with a sufficient tensile strength to push and pull (move or insert) through the patient's spinous process without breaking. In accordance with an exemplary embodiment of the present invention, the IPD tusk-shaped needle 1 comprises at least one of a metal, a ceramic, a plastic, and/or a combination thereof. One of reasonable skill in the art understands that numerous material compositions may be used to produce a curved needle and that all such material compositions are contemplated and disclosed herein.

In accordance with an exemplary embodiment of the present invention, the trailing end 3 of the IPD tusk-shaped needle 1 may be coupled to a guide wire 4 by crimping trailing end 3 around guide wire 4, by soldering trailing end 3 to guide wire 4, by tying guide wire 4 to trailing end 3, and/or any combination thereof. One of reasonable skill in the art understands that numerous means to couple a guide wire to a needle exist and are disclosed herein.

In accordance with an exemplary embodiment of the present invention, guide wire 4 may comprise any material suitable for threading (passing) between a patient's spinous process with a sufficient tensile strength to pull through the patient's spinous process without breaking. Preferably, in accordance with an exemplary embodiment of the present invention, guide wire 4 comprises a steel guide wire. One of reasonable skill in the art understands that numerous guide wires may be used and that all such guide wires are contemplated and disclosed herein.

Additionally, in accordance with an exemplary embodiment of the present invention, guide wire 4 may have an end suitable for detachably coupling to the IP implant device (as discussed below). Preferably, in accordance with an exemplary embodiment of the present invention, guide wire 4 may comprise a threaded end (as denoted by the dark threading at the end of the guide wire 4 in FIG. 1 and as will be described in detail below). One of reasonable skill in the art understands that various guide wire end may be used to couple with an IP implant device and that all such guide wire ends are contemplated and disclosed herein.

In accordance with an exemplary embodiment of the present invention, the insertion end 2 of the IPD tusk-shaped needle 1 may comprise any geometry or shape suitable for percutaneous insertion into a patient's back. Preferably, in accordance with an exemplary embodiment of the present invention, the insertion end 2 of the IPD tusk-shaped needle 1 may comprise a pointed end. One of reasonable skill in the art understands that numerous geometries and shapes may be used to provide for a minimally invasive, percutaneous insertion end 2 and that all such insertion geometries and shapes are contemplated and disclosed herein.

Further, In accordance with an exemplary embodiment of the present invention, the insertion end 2 of the IPD tusk-shaped needle 1 may comprise any geometry or shape suitable for gripping said insertion end 2 upon exit from a patient's back. Preferably, in accordance with an exemplary embodiment of the present invention, the insertion end 2 of the IPD tusk-shaped needle 1 may comprise a receiving hole configured to receive a gripping tool. One of reasonable skill in the art understands that numerous means may be used to provide for gripping insertion end 2 and that all such gripping means are contemplated and disclosed herein.

Further, as illustrated in FIG. 1 and in accordance with an exemplary embodiment of the present invention, the body of the IPD tusk-shaped needle 1 is characterized by the linear width, w, the linear height, h, and an extra length, e, configured to stick out of both the stab incision entrance wound and the exit puncture wound simultaneously. In accordance with an exemplary embodiment of the present invention, the linear height, h, of the body of the IPD tusk-shaped needle 1 may be equal to the distance from the patient's skin to the spinous process. One of reasonable skill in the art understands that determination of the size of the body of the IPD tusk-shaped needle 1 is dependent on patient dimensions. For example, a physician may use experiential data, imaging data (MRI or fluoroscopy), or physical data to estimate the distance from the patient's skin to the spinous process.

Typically, the depth of the spinous process is 3 cm. to 10 cm. Thus, in accordance with an exemplary embodiment of the present invention, the linear height, h, of the IPD tusk-shaped needle 1 may be about 3 cm. to about 10 cm. Preferably, in accordance with an exemplary embodiment of the present invention, h may be about 4 cm. to about 8 cm. Most preferably, in accordance with an exemplary embodiment of the present invention, h may be about 5 cm. to about 6 cm.

Figure 2A:
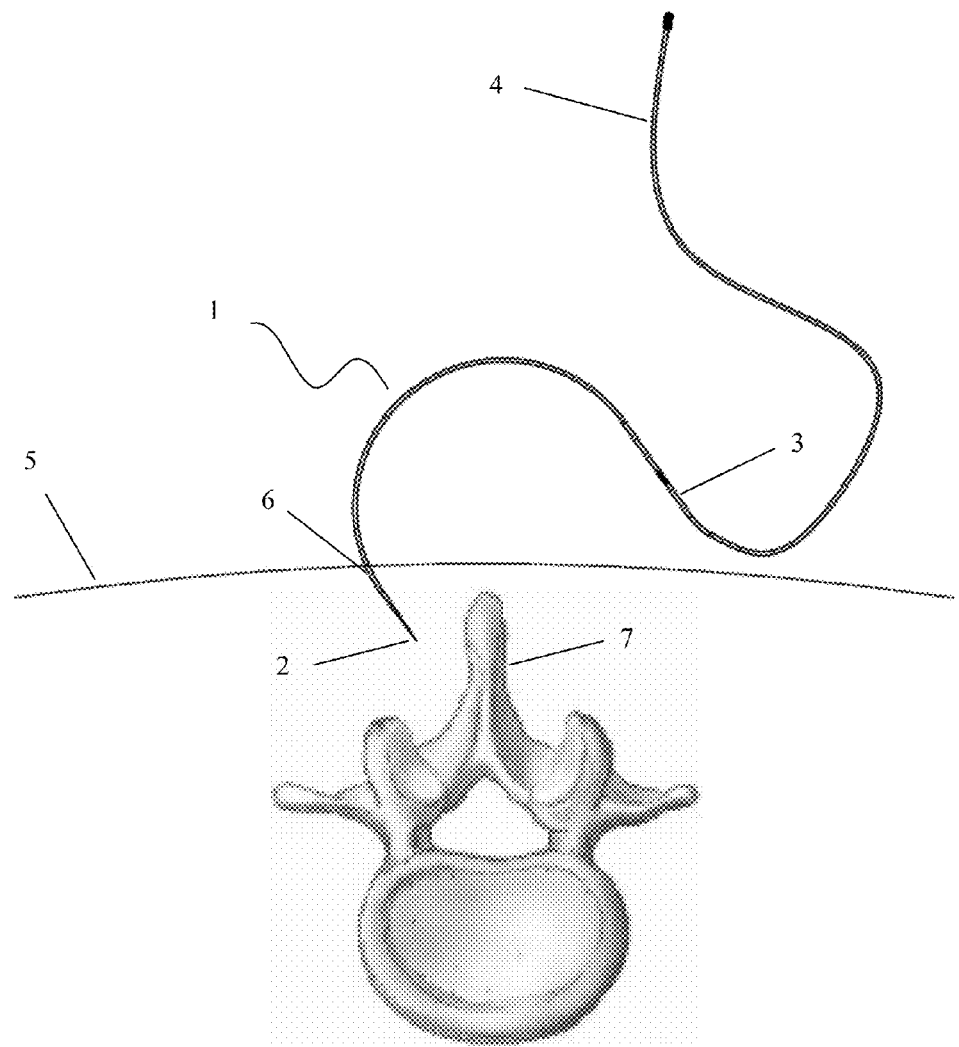
FIG. 2A illustrates a method for inserting an IPD tusk-shaped needle in to a patient's back in accordance with one exemplary embodiment of the present invention.

With reference to FIG. 2A and in accordance with an exemplary embodiment of the present invention, once the physician has determined the distance from the patient's skin 5 to the spinous process 7, an IPD tusk-shaped needle 1 may be selected based on a predetermined h to w ratio. For example, in accordance with an exemplary embodiment of the present invention, the linear width, w, of the IPD tusk-shaped needle 1 may be equal to w=m×h, wherein m is about 1.5 to about 2.5. Preferably, in accordance with an exemplary embodiment of the present invention, m may be about 2.

Further, in accordance with an exemplary embodiment of the present invention, the extra length, e, of the IPD tusk-shaped needle 1 is configured to stick out of both the stab incision entrance wound 6 and the exit puncture wound 8 (shown in FIG. 2B) simultaneously. Preferably, in accordance with an exemplary embodiment of the present invention, the extra length, e, of the IPD tusk-shaped needle 1 may be about 1 cm. to about 3 cm. Most preferably, in accordance with an exemplary embodiment of the present invention, e may be about 2 cm.

Thus, by way of non-limiting example, an IPD tusk-shaped needle 1 may have a linear height, h, of about 5 cm., a linear width, w, of 10 cm. (h=2×5 cm.=10 cm.), and an extra length, e, of 2 cm. This exemplary tusk would have a total height of 7 cm. and a total width of 10 cm.

The spinal stenosis tusk system or kit may comprise three sizes of IPD tusk-shaped needles, small, medium, and large, that will allow for the methods described herein to be performed on the majority of spinal stenosis patients. For example, in accordance with an exemplary embodiment of the present invention, a small IPD tusk-shaped needle may have a linear height, h, of about 3 cm., a linear width, w, of 6 cm. (h=2×3 cm.=6 cm.), and an extra length, e, of 2 cm. This exemplary tusk would have a total height of 5 cm. and a total width of 6 cm. Similarly, a medium IPD tusk-shaped needle may have a linear height, h, of about 5 cm, a linear width, w, of 10 cm. (h=2×5 cm.=10 cm.), and an extra length, e, of 2 cm. This exemplary tusk would have a total height of 7 cm. and a total width of 10 cm.

Again, in accordance with an exemplary embodiment of the present invention, a large IPD tusk-shaped needle may have a linear height, h, of about 7 cm., a linear width, w, of 14 cm. (h=2×7 cm.=14 cm.), and an extra length, e, of 2 cm. This exemplary tusk would have a total height of 9 cm. and a total width of 14 cm.

Alternatively, one of reasonable skill in the art of spinal stenosis surgical procedure will understand that the largest size of the IPD tusk-shaped needle is constrained only by the proximity of the patient's internal organs and care should be taken in using the disclosed IPD tusk-shaped needle. This IPD tusk-shaped needle and surgical procedure may not be appropriate for a large person (i.e. where the distance from the patient's skin 5 to the spinous process 7 is greater than about 10 cm.). The risks associated with the procedure should be assessed by the treating physician for each specific patient.

Figure 2B:
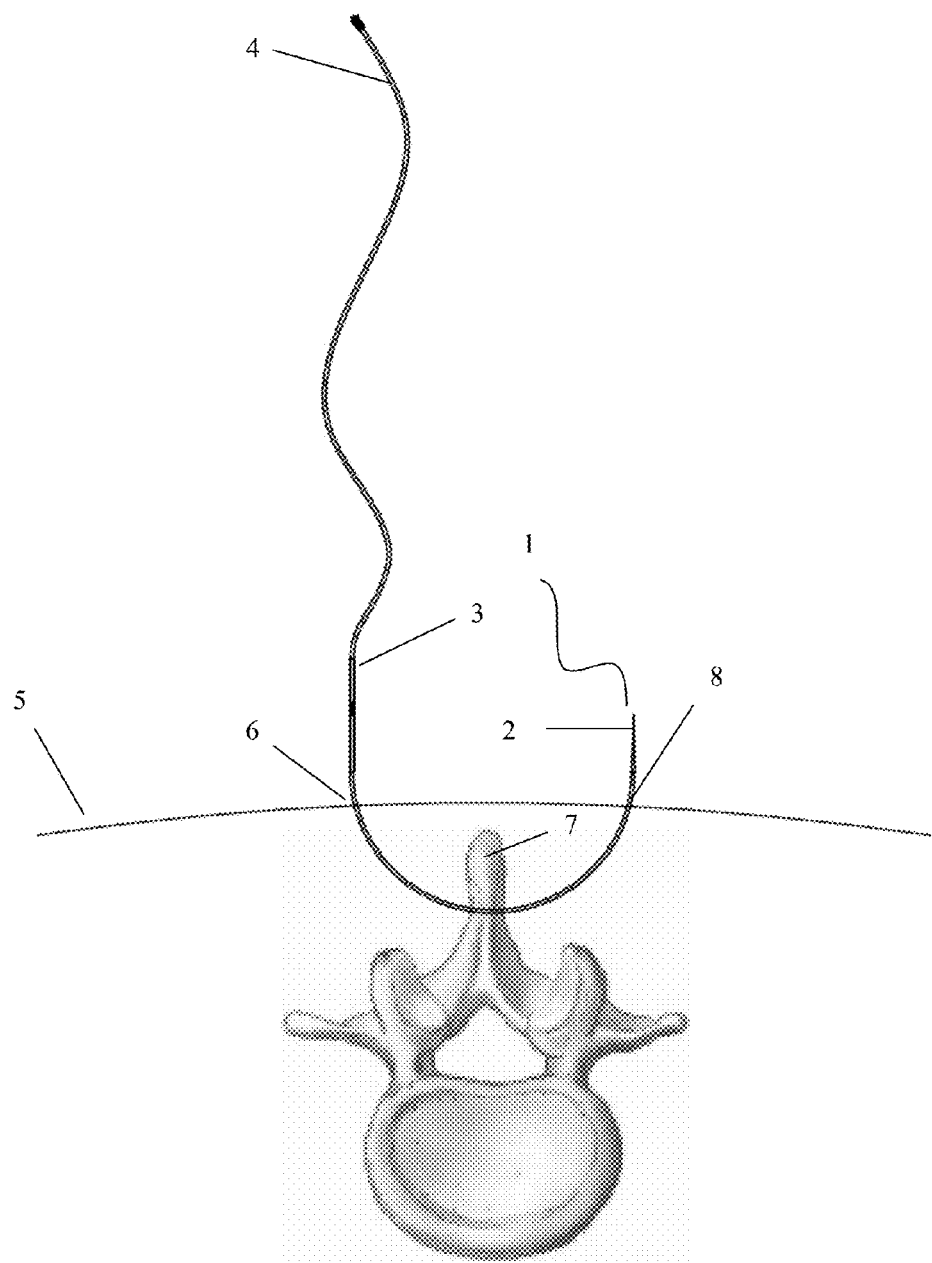
FIG. 2B illustrates a method for inserting an IPD tusk-shaped needle between the patient's spinous process in accordance with one exemplary embodiment of the present invention.

FIG. 2A illustrates the methods for using the tusk-shaped needle 1. In accordance with an exemplary embodiment of the present invention, the IPD tusk-shaped needle 1 is coupled to a guide wire 4 (as discussed above) and percutaneously inserted in the skin on a patient's back 5 via a stab incision 6. The IPD tusk-shaped needle 1 may then be pushed (moved or inserted) and rotated between the patient's spinous process 7. As illustrated in FIG. 2B and in accordance with an exemplary embodiment of the present invention, the IPD tusk-shaped needle 1 is pushed (moved or inserted) and rotated until the insertion end 2 exits the exit puncture wound 8. As discussed above, the IPD tusk-shaped needle 1 is sized such that the trailing end 3 coupled to guide wire 4 protrudes from the stab incision entrance wound 6 while the insertion end 3 simultaneously protrudes from the exit puncture wound 8.

Figure 3:
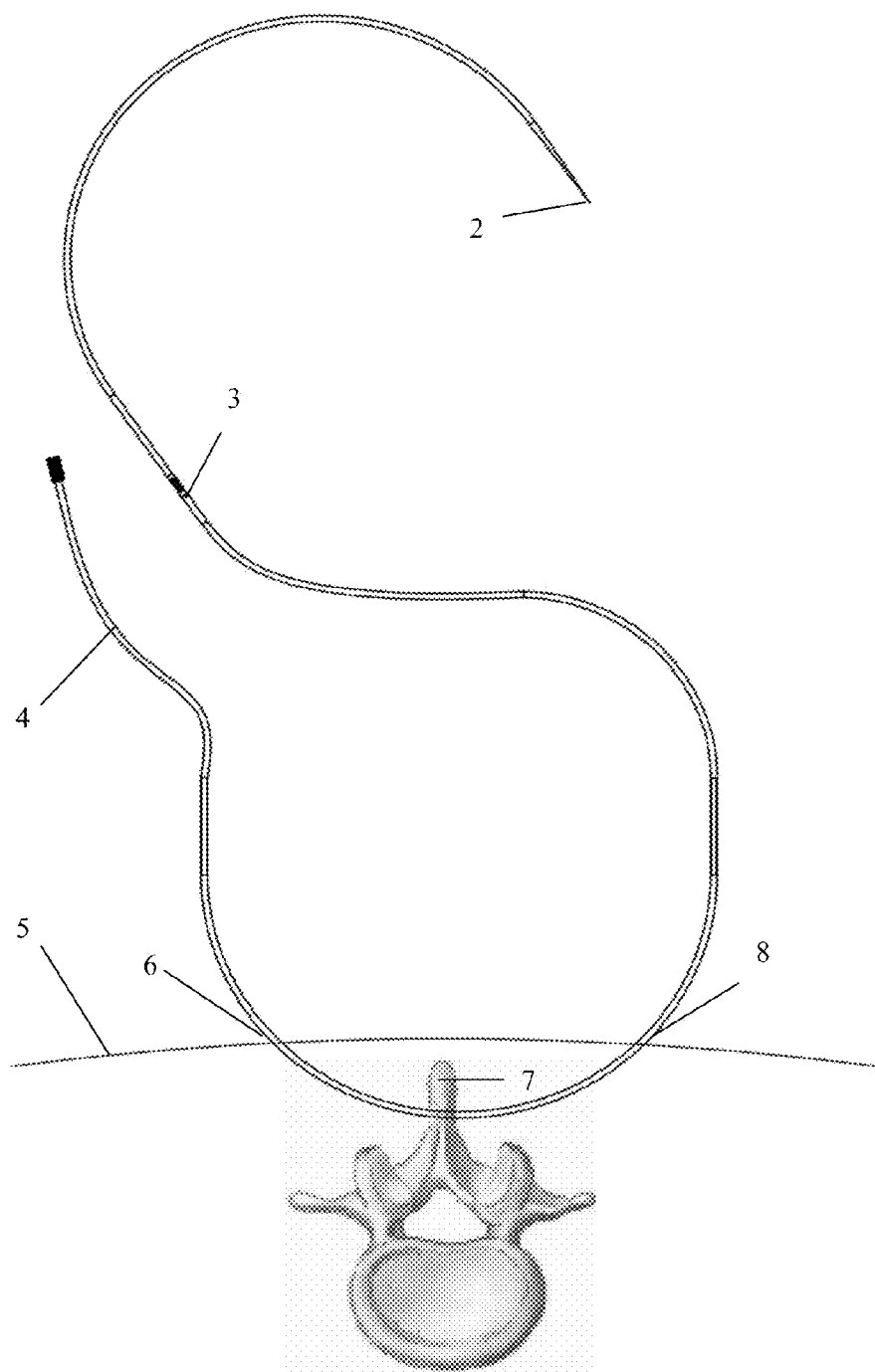
FIG. 3 illustrates a method for inserting a guide wire between the patient's spinous process with an IPD tusk-shaped needle in accordance with one exemplary embodiment of the present invention.

With reference to FIG. 3 and in accordance with an exemplary embodiment of the present invention, once the IPD tusk-shaped needle 1 is pushed (moved or inserted) and rotated between the patient's spinous process 7, the IPD tusk-shaped needle 1 may be gripped from the insertion end 2 by any means and pulled from the patient's back 5 through the exit puncture wound 8. As illustrated in FIG. 3 and in accordance with an exemplary embodiment of the present invention, removal of the IPD tusk-shaped needle 1 leaves the guide wire 4 in the patient's spinous process 7. The guide wire 4 may be used to provide a guide for both the IPD tusk-shaped sizer (shown in FIG. 5A, FIG. 5B, and discussed below) and the IPD tusk-shaped implant tool (shown in FIG. 8, FIG. 9, FIG. 10, and discussed below). One of reasonable skill in the art will understand that the IPD tusk-shaped needle 1 may now be decoupled from the guide wire 4, sterilized, and used for a subsequent operation. Thus, it is within the purview of the instant invention to provide a reusable IPD tusk-shaped needle 1 of varying sizes.

Inter-Spinous Process Decompression (IPD) Tusk-Shaped Sizer Device and Method

Figure 4:
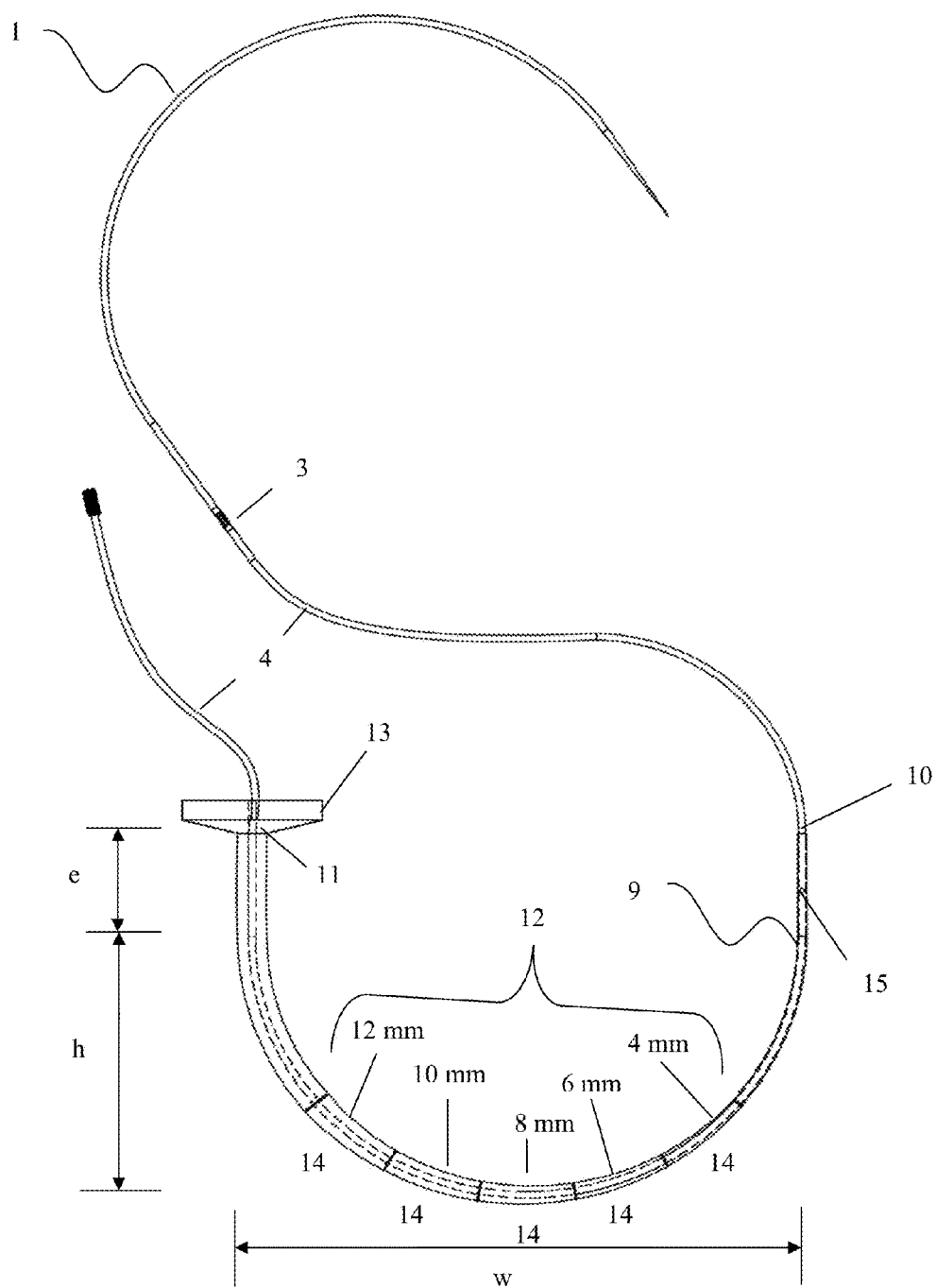
FIG. 4 illustrates an IPD tusk-shaped sizer in accordance with one exemplary embodiment of the present invention.

Once the IPD tusk-shaped needle 1 is removed and the guide wire 4 is in place (as shown in FIG. 3), the patient may be sized for an IPD implant. In accordance with an exemplary embodiment of this invention, the patient's spinous process 7 is sized using an IPD tusk-shaped sizer. As illustrated in FIG. 4 and in accordance with an exemplary embodiment of the present invention, the IPD tusk-shaped sizer 9 comprises a curved, rigid, and cannulated (a hollow channel depicted by dotted lines in FIG. 4) body suitably configured to house a guide wire 4, an insertion end 10 at one end of the body suitable for percutaneous insertion into a patient's back, a trailing end 11 at the opposite end of the body from the insertion end 10, and a measurement region 12 located between the insertion end and the trailing end. Preferably, in accordance with an exemplary embodiment of the present invention, the body of the IPD tusk-shaped sizer 9 may comprise any material suitable for insertion between a patient's spinous process with a sufficient tensile strength to push and pull (move or insert) through the patient's spinous process without breaking or deforming. In accordance with an exemplary embodiment of the present invention, the body of the IPD tusk-shaped sizer 9 may comprises at least one of a metal, a ceramic, a plastic, and/or a combination thereof. One of reasonable skill in the art understands that numerous material compositions may be used to produce a curved sizer and that all such material compositions are contemplated and disclosed herein.

In accordance with an exemplary embodiment of the present invention, the insertion end 10 of the IPD tusk-shaped sizer 9 may comprise any geometry or shape suitable for percutaneous insertion into a patient's back. Preferably, in accordance with an exemplary embodiment of the present invention, the insertion end 10 of the IPD tusk-shaped sizer 9 may comprise a pointed end that allows guide wire 4 to be threaded through it. One of reasonable skill in the art understands that numerous geometries and shapes may be used to provide for a minimally invasive, percutaneous insertion end 10 and that all such insertion geometries and shapes are contemplated and disclosed herein.

Further, In accordance with an exemplary embodiment of the present invention, the insertion end 10 of the IPD tusk-shaped sizer 9 may comprise any geometry or shape suitable for gripping said insertion end 10 upon exit from a patient's back. Preferably, in accordance with an exemplary embodiment of the present invention, the insertion end 10 of the IPD tusk-shaped sizer 9 may comprise a receiving hole configured to receive a gripping tool. One of reasonable skill in the art understands that numerous means may be used to provide for gripping insertion end 10 and that all such gripping means are contemplated and disclosed herein.

Also, in accordance with an exemplary embodiment of the present invention, the trailing end 11 of the IPD tusk-shaped sizer 9 may comprise any geometry or shape suitable for pushing and pulling (moving or inserting) said IPD tusk-shaped sizer 9 into a patient's back and for positioning in a patient's spinous process. Preferably, in accordance with an exemplary embodiment of the present invention, the trailing end 11 of the IPD tusk-shaped sizer 9 may comprise a handle or lip 13 suitably configured to enable/facilitate the pushing and pulling (moving or inserting) the IPD tusk-shaped sizer 9 while between a patient's spinous process. One of reasonable skill in the art understands that numerous means may be used to provide for pushing and pulling (moving or inserting) said IPD tusk-shaped sizer 9 into a patient's back and for positioning in a patient's spinous process and that all such pushing and pulling (moving or inserting) means are contemplated and disclosed herein.

Additionally, in accordance with an exemplary embodiment of the present invention, the IPD tusk-shaped sizer 9 may comprise a coating. In accordance with an exemplary embodiment of the present invention, the IPD tusk-shaped sizer 9 may comprise a coating and/or be pretreated with any substance suitably configured to reduce trauma to the patient's tissue and/or spinous process, to maintain sterility of the device, to reduce inflammation, to protect against infection, to allow for imaging of the individual measurement sections, and/or to provide at least one of an analgesic, an anti-biotic, an anti-inflammatory, a polymeric release agent, an anti-proliferative agent, an anti-thrombotic agent, an anti-migratory agent, an antineoplastic agent, a fibrin growth factor, an anti-bacterial, an anti-mitotic agent, a vascular cell growth inhibitor, a cholesterol-lowering agent, a vasodilating agent, and/or a coagulant (anti-coagulant).

In accordance an exemplary embodiment of the present invention, the protective coating may comprise any biocompatible protective coating. For example, the biocompatible protective coating can include, but is not limited to a biocompatible polymer. The biocompatible polymer may include, but is not limited to, at least one of a polytetrafluoroethylene (PTFE), a polyurethane, a silicone, a polyurethane-urea, and a silicone-polyurethane polymer.

Currently, many biocompatible coatings are commercially available, but due to complex polymeric nature, these compounds are often referred to by their shorthand trade names, including, but not limited to GORE-TEX®, TEFLON®, Dacron®, Pellethane®, a Chronoflex®, a Hydrothane®, an Estane®, an Elast-Eon®, a Texin®, a Biomer®, a Surethane®, a Corethane®, a Carbothane®, a Technoflex®, a Tecothanem®, and a Biospan®.

One of reasonable skill in the art will understand that numerous coatings and pretreatments for medical tools, devices, and implants are known in the art and contemplated herein.

By way of non-limiting example, the curved, rigid, and cannulated body of the IPD tusk-shaped sizer 9 may be made of steel coated in GORETEX® to reduce the coefficient of friction between the IPD tusk-shaped sizer 9 and the patient's tissue. One of reasonable skill in the art understands that numerous material compositions may be used to produce and/or coat a curved, rigid, and cannulated body and that all such material compositions are contemplated and disclosed herein.

In accordance with an exemplary embodiment of the present invention, the curved, rigid, and cannulated body of the IPD tusk-shaped sizer 9 may comprise a labeling material coupled to and/or incorporated inside the IPD tusk-shaped sizer 9. Preferably, in accordance with an exemplary embodiment of the present invention, all or part of IPD tusk-shaped sizer 9 may comprise any labeling material useful for interacting with imaging energy including, but not limited to radiation energy (i.e. X-Rays), electromagnetic energy, sound energy, light energy, and/or any other energy used for therapeutic imaging.

The mechanism by which the label material interacts with the imaging energy is dependent upon the specific material and energy, as will be individually explained below. Additionally, the label material can be suitable metal alloys, suitable piezoelectric materials, and suitable radio-opaque materials. Optionally, in accordance with an exemplary embodiment, the label material may be biocompatible when coupled to and/or incorporated in the patch without an additional external coating.

Non-limiting examples of piezoelectric materials include crystals, including but not limited to at least one of a tourmaline crystal, a quartz crystal, a topaz crystal, a cane sugar crystal, a Rochelle salt crystal; quartz analogue crystals, including but not limited to berlinite ($AlPO_4$), gallium orthophosphate ($GaPO_4$), ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$); and certain polymers, including but not limited to polyvinylidene fluoride, PVDF.

Non-limiting examples of radio-opaque, metal alloy materials include barium, iodine, bralium, bismuth, and/or tungsten.

As mentioned above, in accordance with an exemplary embodiment of the present invention, the energy used to image the labeling material coupled to and/or incorporated inside the IPD tusk-shaped sizer 9 may be any imaging energy used for therapeutic imaging including, but not limited to radiation energy (i.e. X-Rays), electromagnetic energy, sound energy, and/or light energy. One of reasonable skill in the art will appreciate that there are numerous methods for therapeutic imaging, which utilize varying energies and energy waves to form images of patient tissue and implanted devices. As such, said person of reasonable skill will appreciate that such imaging means and energies are contemplated within the scope of this disclosure.

As illustrated in FIG. 4 and in accordance with an exemplary embodiment of the present invention, the measurement region 12 of the IPD tusk-shaped sizer 9 has a gradually increasing diameter with the smallest diameter closest to the insertion end 10 and the largest diameter closest to the trailing end 11. Preferably, in accordance with an exemplary embodiment of the present invention, the measurement region 12 of the IPD tusk-shaped sizer 9 comprises one or more individually measuring segments (by way of non-limiting example these segments are labeled in FIG. 4 as 4 mm. through 12 mm.), which correspond to an IPD implant size. For example, a typical IPD implant can range from about 4 mm. to about 20 mm. One of reasonable skill in the art understands that any number of individually measuring segments in any gradually increasing arrangement are contemplated and disclosed herein.

Most preferably, as illustrated in FIG. 4 and in accordance with an exemplary embodiment of the present invention, the measurement region 12 of the IPD tusk-shaped sizer 9 may comprise a section with a 4 mm. diameter, followed by a section with a 6 mm. diameter, followed by a section with a 8 mm. diameter, followed by a section with a 10 mm. diameter, followed by a section with a 12 mm. diameter. In accordance with an exemplary embodiment of the present invention, the measurement region 12 of the IPD tusk-shaped sizer 9 may continue to increase.

Likened to the whole of the IPD tusk-shaped sizer 9, in accordance with an exemplary embodiment of the present invention, the measurement region 12 may comprise at least one of a metal, a ceramic, a plastic, and/or a combination thereof. As described above, in accordance with an exemplary embodiment of the present invention, the measurement region 12 may comprise any coating, any labeling material, and/or any combination thereof.

As illustrated in FIG. 4 and in accordance with an exemplary embodiment of the present invention, the measurement region 12 may comprise labeling material useful for interacting with imaging energy, wherein the labeling material is used to create at least one of a line and/or a number indicating the size of the individual measuring segments 14.

For example, most commonly, radiation energy can be employed to create X-Rays, which, in turn, allow for imaging of a patient tissue via diagnostic radiography and/or crystallography. Typically, therapeutic X-Rays imaging uses photographic plates and/or a fluoroscope with a wavelength in the range of 0.01 to 10 nanometers, corresponding to frequencies in the range 30 to 30,000 PHz ($10^{15}$ hertz). The radiation energy is able to penetrate patient tissue, but is not able penetrate certain radio-opaque materials, thus these radio-opaque materials interact with the radiation energy by blocking and absorbing the radiation wave energy. This interaction, blocking and absorption, allows the imaging technician to distinguish the radio-opaque material from the surrounding tissue. Accordingly, the measurement region 12 may comprise a radio-opaque label material, as taught above, is disclosed, wherein the radio-opaque label material interacts with the X-Ray energy such that an image of at least one line and/or number 14 indicating the size of the individual measuring segments can be imaged.

Similarly, in accordance with an exemplary embodiment of the present invention, magnetic or electromagnetic energy can be employed to create both passive and dynamic electric fields, which, in turn, allow for imaging of a patient tissue via therapeutic magnetic resonance imaging (MRI or sometimes referred to as magnetic resonance tomography, "MRT"). MRI is a method for imaging tissue by subjecting the tissue to multiple passive magnetic fields, such that the tissue is polarized along a given axis (x, y, or z), subsequently a dynamic electromagnetic field is introduced along an axis to excite the tissue, thereby allowing for detailed images to be acquired. Common magnetic field strengths range from 0.3 to 3 tesla (T), although field strengths as high as 9.4 T or higher are used in research scanners and research instruments for animals or only small test tubes range as high as 20 T. As such, it is well known in the art that different materials interact to differing extents with the MRI electromagnetic field energy. For example, magnetic (i.e. ferrous) metals can be problematic due to the strong interaction with the electromagnetic energy used in MRI. Notwithstanding the foregoing, other label materials are useful for imaging and/or providing an internal reference for the MRI operator. Such materials interact with the electromagnetic energy, both passive and dynamic electric fields, used in MRI to a greater extent than the patient tissue. Accordingly, in accordance with an exemplary embodiment of the present invention, the measurement region 12 may comprise a magnetic or electromagnetic label material, as taught above, wherein the magnetic or electromagnetic label material interacts with magnetic or electromagnetic energy such that an image of at least one line and/or number 13 indicating the size of the individual measuring segments can be imaged.

In another exemplary embodiment, light energy via light wave refraction and/or absorption can be employed to image subcutaneous medical devices. It is well established in the art that various wavelengths of light penetrate human epithelial tissue (skin) at differing depths. Typically, light imaging is being researched using light in the infrared range, 750 nanometers to 1 mm, and preferably 830 to 850 nanometers. As such, it is well known in the art that different materials interact differently to light energy. For example, different materials refraction and/or absorption light wave energy at differing levels. Thus, in accordance with an exemplary embodiment of the present invention, the measurement region 12 may comprise label material to refract and/or absorb light wave energy such that an image of at least one line and/or number 13 indicating the size of the individual measuring segments can be imaged.

Likened to the IPD tusk-shaped needle 1, as illustrated in FIG. 4 and in accordance with an exemplary embodiment of the present invention, the IPD tusk-shaped sizer 9 is characterized by the linear width, w, the linear height, h, and an extra length, e, configured to stick out of both the stab incision entrance wound and the exit puncture wound simultaneously. In accordance with an exemplary embodiment of the present invention, the linear height, h, of the IPD tusk-shaped sizer 9 may be equal to the distance from the patient's skin to the spinous process. One of reasonable skill in the art understands that determination of the size of the IPD tusk-shaped sizer 9 is dependent on patient dimensions. For example, a physician may use experiential data, imaging data (MRI or fluoroscopy), or physical data to estimate the distance from the patient's skin to the spinous process.

As discussed above, in accordance with an exemplary embodiment of the present invention, the linear height, h, of the IPD tusk-shaped sizer 9 may be about 3 cm. to about 10 cm. Preferably, in accordance with an exemplary embodiment of the present invention, h may be about 4 cm. to about 8 cm. Most preferably, in accordance with an exemplary embodiment of the present invention, h may be about 5 cm. to about 6 cm. Similarly, in accordance with an exemplary embodiment of the present invention, the linear width, w, of the IPD tusk-shaped sizer 9 may be equal to w=m×h, wherein m is about 1.5 to about 2.5. Preferably, in accordance with an exemplary embodiment of the present invention, m may be about 2.

Likened to the IPD tusk-shaped needle 1, in accordance with an exemplary embodiment of the present invention, the extra length, e, of the IPD tusk-shaped sizer 9 may be configured to stick out of both the stab incision entrance wound and the exit puncture wound simultaneously. Preferably, in accordance with an exemplary embodiment of the present invention, the extra length, e, of the IPD tusk-shaped sizer 9 may be about 1 cm. to about 3 cm. Most preferably, in accordance with an exemplary embodiment of the present invention, e may be about 2 cm.

One of reasonable skill in the art of spinal stenosis surgical procedure will understand that a spinal stenosis tusk system or kit may comprise three sizes of IPD tusk-shaped sizers, small, medium, and large, that will allow for the methods described herein to be performed on the majority of spinal stenosis patients. Like the IPD tusk-shaped needles, in accordance with an exemplary embodiment of the present invention, a small IPD tusk-shaped sizer 9 may have a linear height, h, of about 3 cm., a linear width, w, of 6 cm. (h=2×3 cm.=6 cm.), and an extra length, e, of 2 cm. This exemplary tusk would have a total height of 5 cm. and a total width of 6 cm. A medium IPD tusk-shaped sizer 9 may have a linear height, h, of about 5 cm, a linear width, w, of 10 cm. (h=2×5 cm.=10 cm.), and an extra length, e, of 2 cm. This exemplary tusk would have a total height of 7 cm. and a total width of 10 cm.

Again, in accordance with an exemplary embodiment of the present invention, a large IPD tusk-shaped sizer 9 may have a linear height, h, of about 7 cm., a linear width, w, of 14 cm. (h=2×7 cm.=14 cm.), and an extra length, e, of 2 cm. This exemplary tusk would have a total height of 9 cm. and a total width of 14 cm.

Alternatively, one of reasonable skill in the art of spinal stenosis surgical procedure will understand that the largest size of the IPD tusk-shaped sizer 9 is constrained only by the proximity of the patient's internal organs and care should be taken in using the disclosed IPD tusk-shaped needle. This IPD tusk-shaped sizer and surgical procedure may not be appropriate for a large person (i.e. where the distance from the patient's skin 5 to the spinous process 7 is greater than about 10 cm.).

In another exemplary embodiment, the IPD tusk-shaped sizer 9 comprises a trailing end 11 suitable for gripping, preferably with a tusk gripping tool (shown in FIG. 10 and discussed below). With reference to FIG. 4, in accordance with an exemplary embodiment of the present invention, the trailing end 11 suitable for gripping may comprise any means for gripping the IPD tusk-shaped sizer 9 including, but not limited to a "T" handle grip, gripping lip 13, and/or a bored hole configured for receiving a tool (not shown). One of reasonable skill in the art will appreciate that there are numerous means for coupling a tool to the trailing end 11 of the IPD tusk-shaped sizer 9 and will understand that all of these means for coupling and gripping are contemplated within the scope of this disclosure.

Again, with reference to FIG. 4 and in accordance with an exemplary embodiment of the present invention, the insertion end 10 may comprise any means for securing the guide wire 4 within the curved, rigid, and cannulated body of the IPD tusk-shaped sizer 9. Preferably, in accordance with an exemplary embodiment of the present invention, the means for securing the guide wire 4 within the curved, rigid, and cannulated body of the IPD tusk-shaped sizer 9 may comprise a set screw 15, wherein the set screw may be tightened to secure the guide wire 4 in place in order to allow a physician to pull on the IPD tusk-shaped sizer 9 by pulling on the guide wire 4. One of reasonable skill in the art will appreciate that there are numerous means for securing the guide wire 4 to the IPD tusk-shaped sizer 9 and will understand that all of these means for coupling and gripping are contemplated within the scope of this disclosure.

Figure 5A:
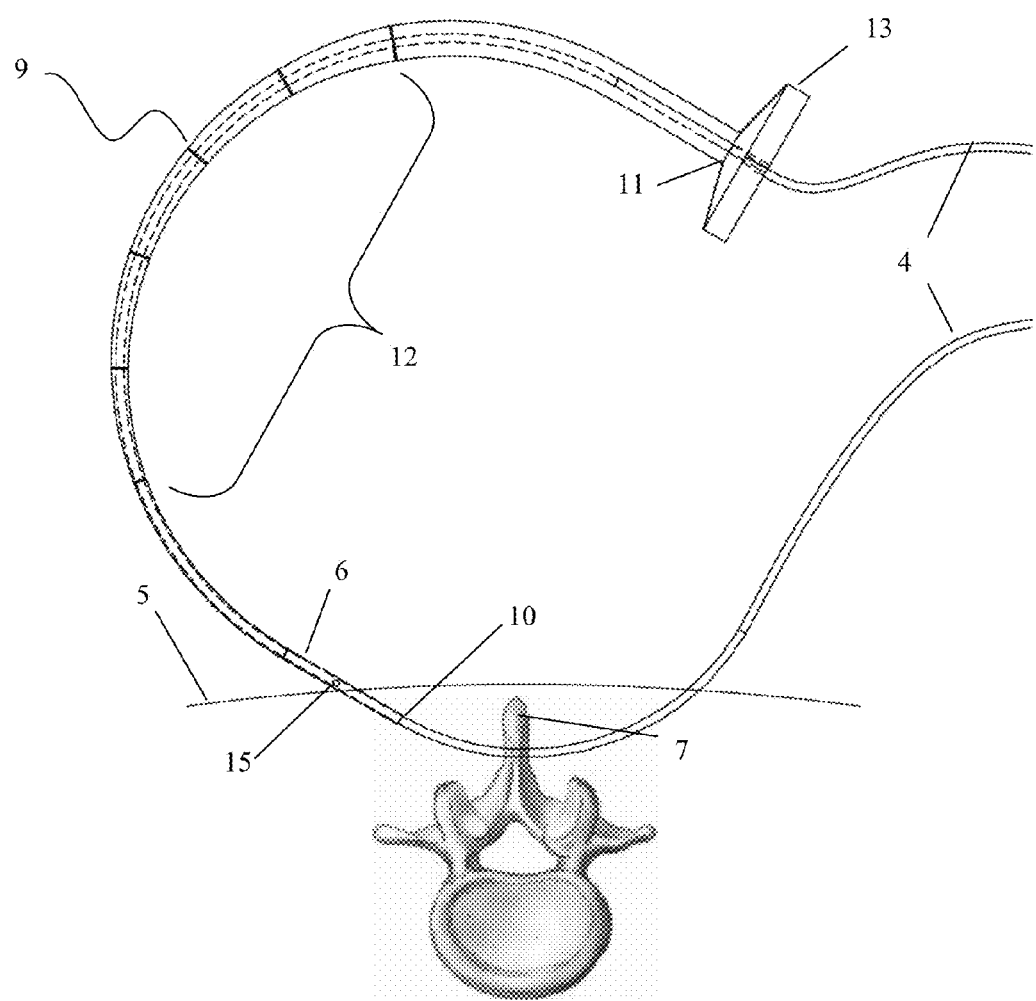
FIG. 5A illustrates a method for inserting an IPD tusk-shaped sizer between the patient's spinous process in accordance with one exemplary embodiment of the present invention.

FIG. 5A illustrates a method for using an IPD tusk-shaped sizer 9. Initially, in accordance with an exemplary embodiment of the present invention, IPD tusk-shaped sizer 9 is placed around the guide wire 4 (guide wire 4 is passed through the IPD tusk-shaped sizer 9) and percutaneously inserted in the skin on a patient's back 5 via a stab incision 6 (as discussed above). Preferably, in accordance with an exemplary embodiment of the present invention, the set screw 15 in the insertion end 10 may be tightened to secure the guide wire 4 and lock the IPD tusk-shaped sizer 9 in place.

Figure 5B:
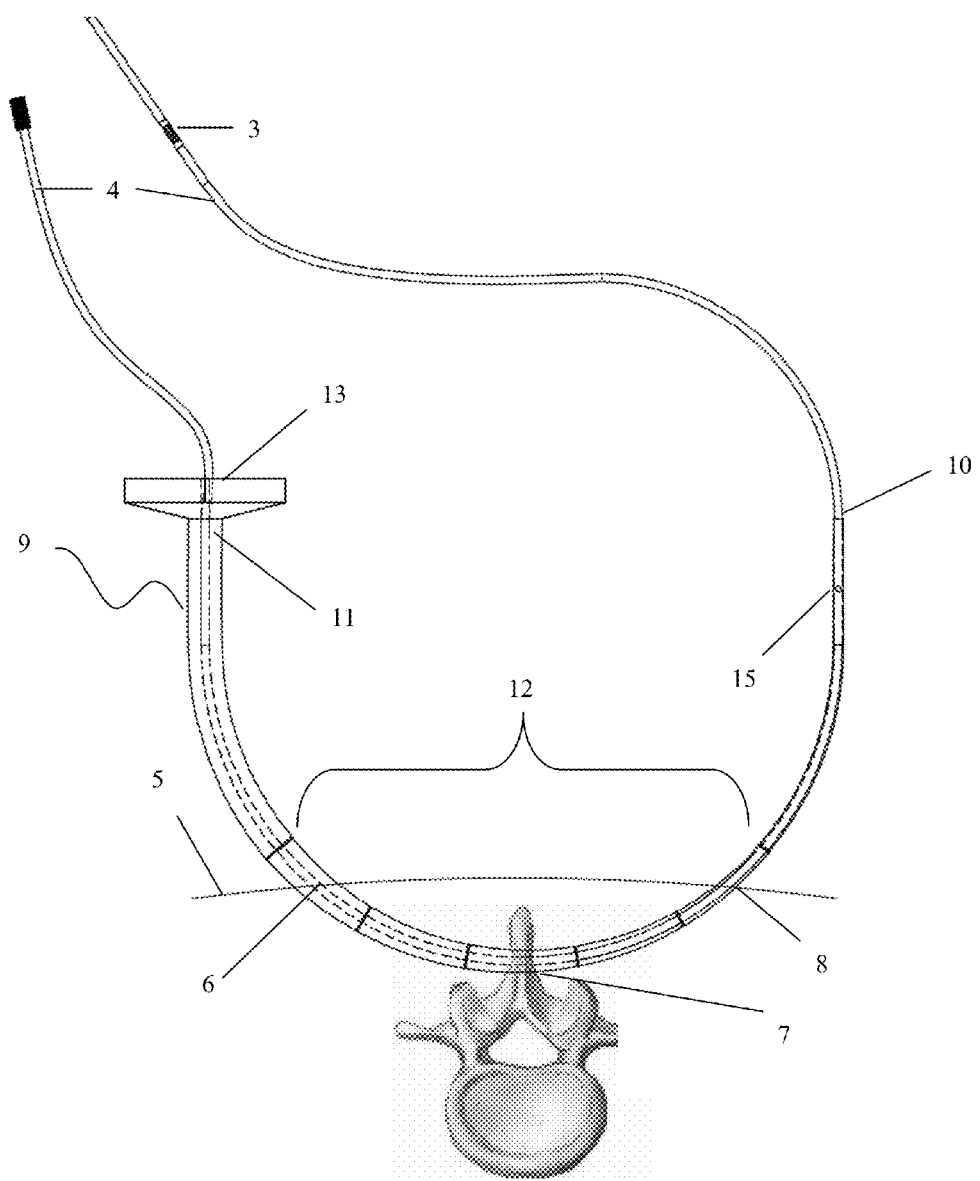
FIG. 5B illustrates a method for determining the size of an IPD implant for a given patient's spinous process with an IPD tusk-shaped sizer in accordance with one exemplary embodiment of the present invention.

Following the same path as the guide wire 4, the IPD tusk-shaped sizer 9 may then be pushed on the trailing end 11 and/or pulled from the insertion end 10 by pulling on the guide wire 4 and rotated between the patient's spinous process 7. With reference to FIG. 5B and in accordance with an exemplary embodiment of the present invention, the IPD tusk-shaped sizer 9 is pushed and/or pulled (moved or inserted) between the patient's spinous process 7 until the physician determines that the patient's spinous process 7 is adequately dilated. One of reasonable skill in the art understands that determination of the sizing for an IPD implant may depend on physician experience, imaging data (MRI or fluoroscopy), and/or physical data (pushing/pulling/moving/inserting to determine dilation and tissue rigidity).

Preferably, in accordance with an exemplary embodiment of the present invention, the IPD tusk-shaped sizer 9 is pushed and/or pulled (moved or inserted) between the patient's spinous process 7 and fluoroscopic images are taken at different intervals to determine the proper amount of spinous process dilation and to determine the sizing for an IPD implant. In accordance with an exemplary embodiment of the present invention, the IPD tusk-shaped sizer 9 is pushed and/ or pulled (moved or inserted) between the patient's spinous process 7 and as fluoroscopic images the labeled segments in the measurement region 12 provide a visual reference and real-time measurement of the spinous process dilation. This measurement of the spinous process dilation is preferably then used to determine the size of the IPD implant to be used.

In accordance with an exemplary embodiment of the present invention, the IPD tusk-shaped sizer 9 is configured to stick out of both the stab incision entrance wound and the exit puncture wound simultaneously prior to measurement region 12 entering the patient's spinous process 7.

Inter-Spinous Process Decompression (IPD) Implant Device and Method

Once the spinous process 7 is sufficiently dilated and the IPD implant size is determined for the patient, the IPD tusk-shaped sizer 9 may be either partially or fully removed. In an exemplary embodiment of the present invention, the IPD tusk-shaped sizer 9 may be partially removed and used an IPD tusk-shaped implant tool. For example, in one exemplary embodiment of the present invention, after the IPD implant size is determined for the patient, the IPD tusk-shaped sizer 9 may be partially pulled out of the patient (toward the stab incision 6) until the measuring segment 14 corresponding to the IPD implant size in the measurement region 12 in (with reference to FIG. 4) is out of the stab incision 6 (as discussed above). Then, in accordance with the present invention, all measuring segments 14 larger, greater in diameter, than the determined IPD implant size may be removed. Stated another way, in an exemplary embodiment of the present invention, each measuring segment 14 is detachably coupled to a measuring segment 14 with a smaller diameter located closer to the insertion end 10 and a measuring segment 14 with a larger diameter located closer to the trailing end 11. Thus, in an exemplary embodiment of the present invention, the IPD tusk-shaped sizer 9 may be backed out of the stab incision 6 and all measuring segments 14 larger than the determined implant size can be detached and replaced with an IPD implant (the exemplary methods and structures for detaching or attaching the IPD implant to the IPD tusk-shaped implant tool are described below with reference to FIG. 7).

Most preferably, in accordance with an exemplary embodiment of the present invention, after the preferred spinous process dilation measurement is determined and the size of the IPD implant is determined, the IPD tusk-shaped sizer 9 may be fully removed from the spinous process 7 and the patient's back by backing out the IPD tusk-shaped sizer 9 form the stab incision 6 in the patient's skin and by leaving the guide wire 4 in place to provide a path from the stab incision 6 through the patient's spinous process 7 and out the exit puncture wound 8 (See detailed description of IPD procedures below).

One of reasonable skill in the art will understand that the IPD tusk-shaped sizer 9 may be decoupled from the guide wire 4, sterilized, and used for a subsequent operation. Thus, it is within the purview of the instant invention to provide a reusable IPD tusk-shaped sizer 9.

Figure 6:
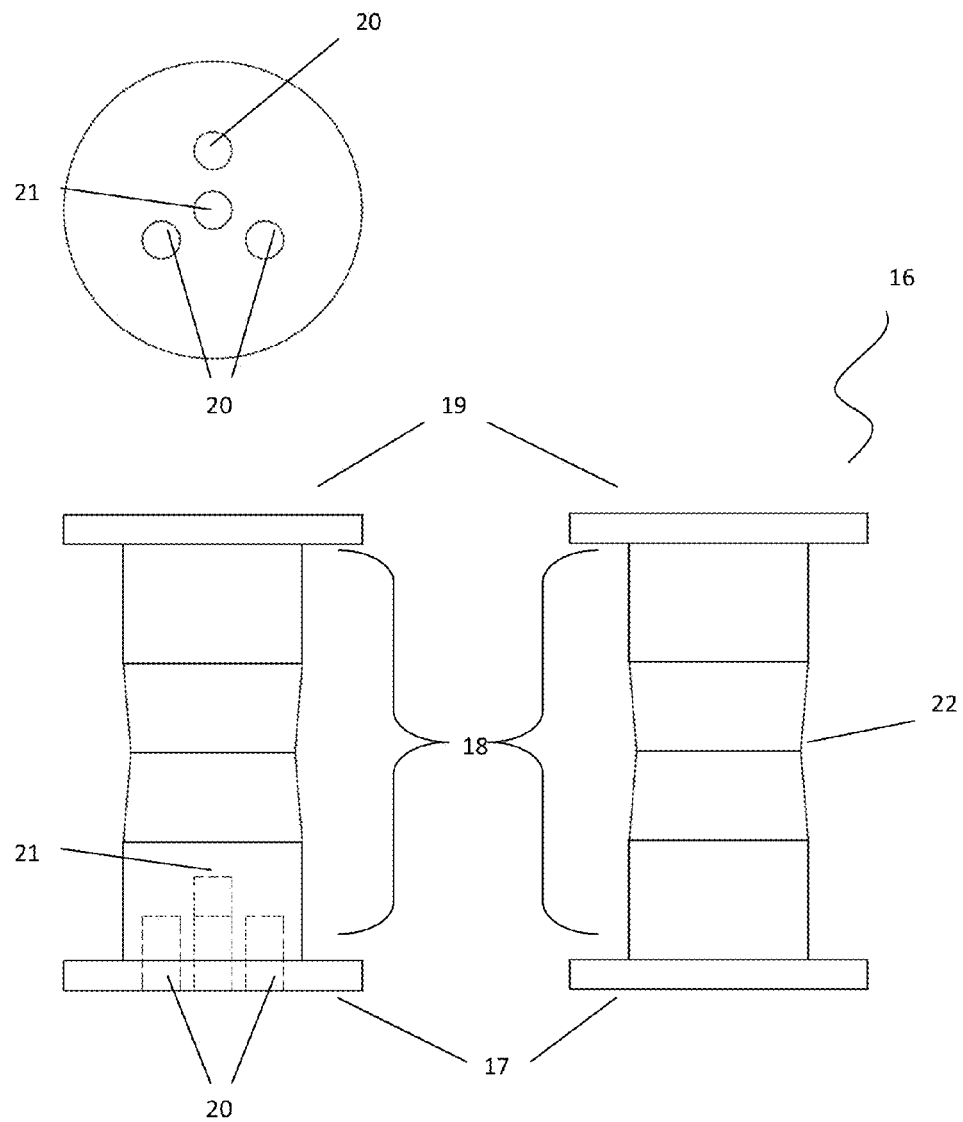
FIG. 6 illustrates an IPD implant in accordance with one exemplary embodiment of the present invention.

As illustrated in FIG. 6 and in accordance with an exemplary embodiment of the present invention, the IPD implant 16 may comprise a leading edge 17 suitably configured to couple to either the IPD tusk-shaped sizer 9 or the IPD tusk-shaped implant tool (described below with reference to FIG. 7), a middle portion 18 between the leading edge and the following edge, wherein the middle portion 18 is suitably configured to dilate and maintain separation of the patient's spinous process 7, and a following edge 19. Preferably, in accordance with an exemplary embodiment of the present invention, both the leading edge 17 and the following edge 19 of the IPD implant 16 has a diameter equal to or less than the diameter of the measuring segment 14 corresponding to the determined IPD implant size (as described above) or the trailing end of the IPD tusk-shaped implant tool (described below with reference to FIG. 7). Most preferably, as illustrated in FIG. 6 and in accordance with an exemplary embodiment of the present invention, the IPD implant 16 may be shaped likened to a spool of thread. One of reasonable skill in the art will appreciate that there are numerous shapes and geometries that can be employed in connection with an IPD implant and understand that any shape and/or geometry suitable for dilating and maintaining separation of the patient's spinous process 7 are contemplated within the scope of this disclosure.

In accordance with an exemplary embodiment of the present invention, the leading edge 17 of the IPD implant 16 may comprise any means for coupling the IP implant 16 to either the IPD tusk-shaped sizer 9 or the IPD tusk-shaped implant tool (described below with reference to FIG. 7). Preferably, in accordance with an exemplary embodiment of the present invention, the leading edge 17 of the IPD implant 16 may comprise one or more locating female receivers 20 suitable for receiving one or more locating pins (not shown) on either the IPD tusk-shaped sizer 9 or the IPD tusk-shaped implant tool (described below with reference to FIG. 7). In these exemplary embodiments, the leading edge 17 of the IPD implant 16 may additionally comprise a threaded female channel 21 suitable for receiving a threaded end of a guide wire 4. One of reasonable skill in the art will appreciate that there are numerous means for coupling an IPD implant to either the IPD tusk-shaped sizer or the IPD tusk-shaped implant tool and will understand that all of these means for coupling are contemplated within the scope of this disclosure.

Further, as illustrated in FIG. 6 and in accordance with an exemplary embodiment of the present invention, the middle portion 18 of the IPD implant 16 may have an outer diameter of about 2 mm to about 14 mm. More preferably, the middle portion 18 of the IPD implant 16 may have an outer diameter of about 4 mm to about 12 mm. Most preferably, the outer diameter of middle portion 18 of the IPD implant 16 is equal to the appropriate spinous process size determined by the IPD tusk-shaped sizer 9 (as described above).

Preferably, as illustrated in FIG. 6 and in accordance with an exemplary embodiment of the present invention, the outer diameter of the leading edge 17 and following edge 19 of the IPD implant 16 may be about 0.5 mm to about 2.5 mm larger than the middle portion 18 of the IPD implant 16. More preferably, in accordance with an exemplary embodiment of the present invention, the outer diameter of the leading edge 17 and following edge 19 of the IPD implant 16 may be about 1 mm to about 2 mm larger than the middle portion 18 of the IPD implant 16. Most preferably, in accordance with an exemplary embodiment of the present invention, the outer diameter of the leading edge 17 and following edge 19 of the IPD implant 16 may be about 1.5 mm larger than the middle portion 18 of the IPD implant 16.

Additionally, in accordance with an exemplary embodiment of the present invention, the outer diameter of the middle portion 18 of the IPD implant 16 may change from the leading edge 17 and following edge 19. For example, the outer diameter of the middle portion 18 of the IPD implant 16 may taper to a minimum 22 as shown in FIG. 6 or bulge to a maximum (not shown). One of reasonable skill in the art will understand that any change of diameter of the middle portion 18 suitable to maintain the spacing in the spinous process and to allow the spinous process to contract around the a middle portion 18 is contemplated herein.

One of reasonable skill in the art will understand that the leading edge 17, middle portion 18, and following edge 19 with various diameters are known in the art and contemplated herein.

The present application contemplates various geometries and shapes for the detachable IPD implant 16, but all of these shapes are suitably configured for maintain the spacing in the spinous process created by the IPD tusk-shaped sizer 9 or the IPD tusk-shaped implant tool (described below with reference to FIG. 7) and then allowing the spinous process to contract around the a middle portion 18 with a diameter less than the diameter of the leading edge 17, and having a following edge 19 with the same diameter of the leading edge 17 to hold the IPD implant 16 within the spinous process.

Additionally, in accordance with an exemplary embodiment of the present invention, the IPD implant 16 may comprise a coating. In accordance with an exemplary embodiment of the present invention, the IPD implant 16 may comprise a coating and/or be pretreated with any substance suitably configured to reduce trauma to the patient's tissue and/or spinous process, to maintain sterility of the device, to reduce inflammation, to protect against infection, to allow for imaging of the individual measurement sections, and/or to provide at least one of an analgesic, an anti-biotic, an anti-inflammatory, a polymeric release agent, an anti-proliferative agent, an anti-thrombotic agent, an anti-migratory agent, an antineoplastic agent, a fibrin growth factor, an anti-bacterial, an anti-mitotic agent, a vascular cell growth inhibitor, a cholesterol-lowering agent, a vasodilating agent, and/or a coagulant (anti-coagulant). In accordance with an exemplary embodiment of the present invention, the IPD implant 16 may have a coating comprising bone. Preferably, in accordance with an exemplary embodiment of the present invention, the IPD implant 16 may have a coating comprising bone and a bone adhesion agent. This combination may allow for the IPD implant 16 to be adhered/fused to the patient's bone in accordance with the procedure defined herein.

In accordance an exemplary embodiment of the present invention, the protective coating may comprise any biocompatible protective coating. For example, the biocompatible protective coating can include, but is not limited to a biocompatible polymer. The biocompatible polymer may include, but is not limited to, at least one of a polytetrafluoroethylene (PTFE), a polyurethane, a silicone, a polyurethane-urea, and a silicone-polyurethane polymer.

Currently, many biocompatible coatings are commercially available, but due to complex polymeric nature, these compounds are often referred to by their shorthand trade names, including, but not limited to GORE-TEX®, TEFLON®, Dacron®, Pellethane®, a Chronoflex®, a Hydrothane®, an Estane®, an Elast-Eon®, a Texin®, a Biomer®, a Surethane®, a Corethane®, a Carbothane®, a Technoflex®, a Tecothanem®, and a Biospan®.

One of reasonable skill in the art will understand that numerous coatings and pretreatments for medical tools, devices, and implants are known in the art and contemplated herein.

Preferably, in accordance with an exemplary embodiment of the present invention, all or part of IPD implant 16 may comprise any labeling material useful for interacting with imaging energy including, but not limited to radiation energy (i.e. X-Rays), electromagnetic energy, sound energy, light energy, and/or any other energy used for therapeutic imaging.

The mechanism by which the label material interacts with the imaging energy is dependent upon the specific material and energy, as will be individually explained below. Additionally, the label material can be suitable metal alloys, suitable piezoelectric materials, and suitable radio-opaque materials. Optionally, in accordance with an exemplary embodiment, the label material may be biocompatible when coupled to and/or incorporated in the patch without an additional external coating.

Non-limiting examples of piezoelectric materials include crystals, including but not limited to at least one of a tourmaline crystal, a quartz crystal, a topaz crystal, a cane sugar crystal, a Rochelle salt crystal; quartz analogue crystals, including but not limited to berlinite ($AlPO_4$), gallium orthophosphate ($GaPO_4$), ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$); and certain polymers, including but not limited to polyvinylidene fluoride, PVDF.

Non-limiting examples of radio-opaque, metal alloy materials include barium, iodine, bralium, bismuth, and/or tungsten.

As mentioned above, in accordance with an exemplary embodiment of the present invention, the energy used to image the labeling material coupled to and/or incorporated inside the IPD implant 16 may be any imaging energy used for therapeutic imaging including, but not limited to radiation energy (i.e. X-Rays), electromagnetic energy, sound energy, and/or light energy. One of reasonable skill in the art will appreciate that there are numerous methods for therapeutic imaging, which utilize varying energies and energy waves to form images of patient tissue and implanted devices. As such, said person of reasonable skill will appreciate that such imaging means and energies are contemplated within the scope of this disclosure.

By way of other non-limiting example, in accordance with an exemplary embodiment of the present invention, the whole of the IPD implant 16 may comprise at least one of a metal, a ceramic, a plastic, bone, and/or a combination thereof. One of reasonable skill in the art will understand that numerous materials for medical tools, devices, and implants are known in the art and contemplated herein.

Inter-Spinous Process Decompression (IPD) Tusk-Shaped Implant Tool and Method

As mentioned above, in a preferred embodiment of the present invention, the IPD implant 16 is reversibly coupled to an IPD tusk-shaped implant tool 23. Specifically, in an exemplary embodiment of the present invention, once the spinous process 7 is sufficiently dilated and the IP implant size is determined for the patient, the IPD tusk-shaped sizer 9 may be fully removed, the determined size of the IPD implant 16 may be coupled to the IPD tusk-shaped implant tool 23, and the IPD tusk-shaped implant tool 23 may be reinserted in to the stab incision 6 along the path of the guide wire 4.

Figure 7:
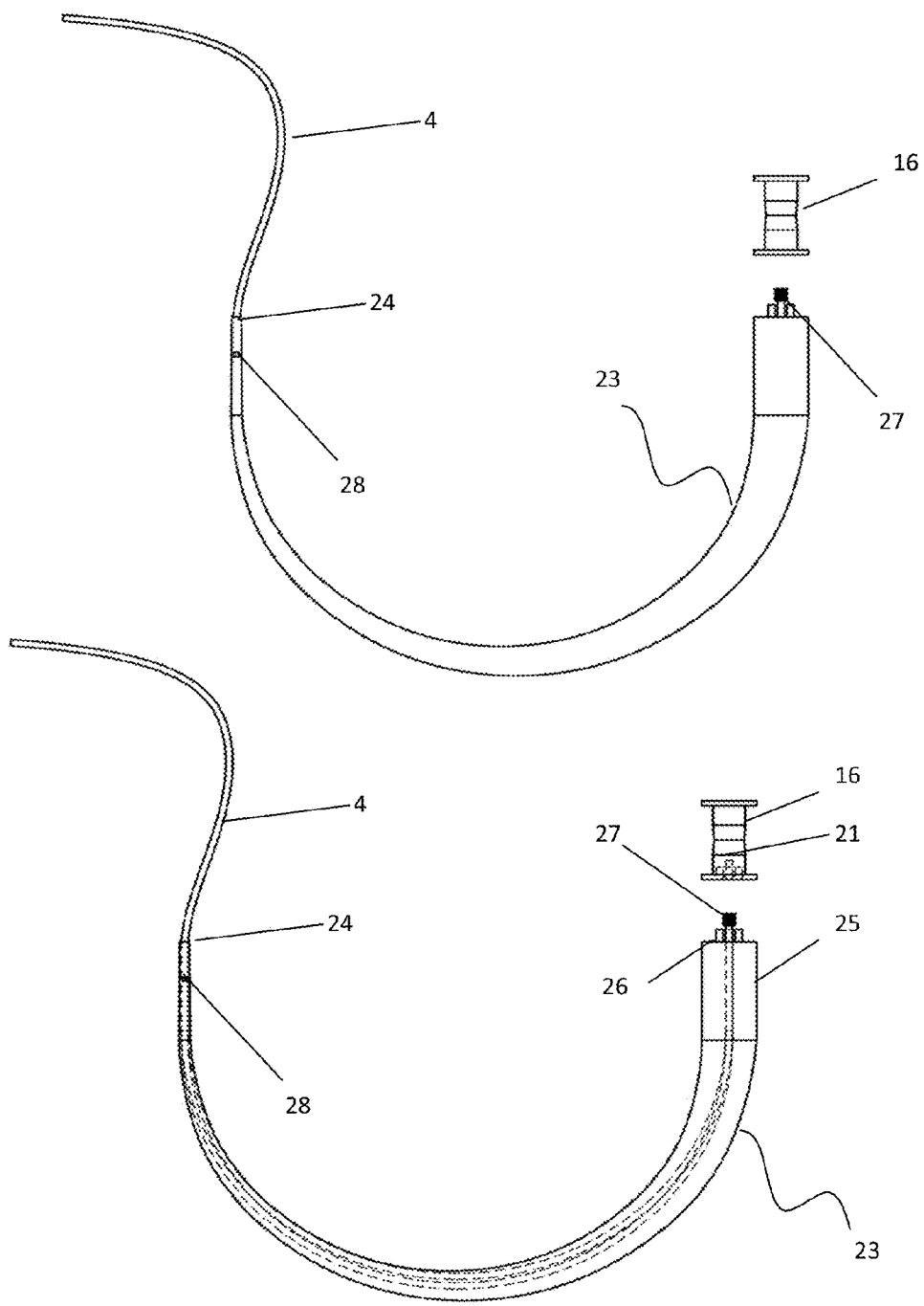
FIG. 7 illustrates an IPD tusk-shaped implant tool coupled to an IPD implant in accordance with one exemplary embodiment of the present invention.

As illustrated in FIG. 7 and in accordance with an exemplary embodiment of the present invention, the IPD tusk-shaped implant tool 23 may comprise a curved, rigid, and cannulated (a hollow channel depicted by dotted lines in FIG. 7) body suitably configured to house a guide wire 4, an insertion end 24 at one end of the body suitable for percutaneous insertion into a patient's back, and a trailing end 25 at the opposite end of said body 23 from the insertion end 24 suitably configured to couple and locate the IPD implant 16.

Preferably, in accordance with an exemplary embodiment of the present invention, the IPD tusk-shaped implant tool 23 may comprise any material suitable for insertion between a patient's spinous process with a sufficient tensile strength to push and pull (move or insert) through the patient's spinous process without breaking or deforming. In accordance with an exemplary embodiment of the present invention, the IPD tusk-shaped implant tool 23 may comprise at least one of a metal, a ceramic, a plastic, and/or a combination thereof. One of reasonable skill in the art understands that numerous material compositions may be used to produce a curved sizer and that all such material compositions are contemplated and disclosed herein.

In accordance with an exemplary embodiment of the present invention, the insertion end 24 of the IPD tusk-shaped implant tool 23 may comprise any geometry or shape suitable for percutaneous insertion into a patient's back. Preferably, in accordance with an exemplary embodiment of the present invention, the insertion end 24 of the IPD tusk-shaped implant tool 23 may comprise a pointed end that allows guide wire 4 to be threaded through it. One of reasonable skill in the art understands that numerous geometries and shapes may be used to provide for a minimally invasive, percutaneous insertion end 24 and that all such insertion geometries and shapes are contemplated and disclosed herein.

Further, in accordance with an exemplary embodiment of the present invention, the insertion end 24 of the IPD tusk-shaped implant tool 23 may comprise any geometry or shape suitable for gripping said insertion end 24 upon exit from a patient's back. Preferably, in accordance with an exemplary embodiment of the present invention, the insertion end 24 of the IPD tusk-shaped implant tool 23 may comprise a receiving hole configured to receive a gripping tool. One of reasonable skill in the art understands that numerous means may be used to provide for gripping insertion end 24 and that all such gripping means are contemplated and disclosed herein.

Also, in accordance with an exemplary embodiment of the present invention, the trailing end 25 of the IPD tusk-shaped implant tool 23 may comprise any geometry or shape suitable for orientating the IPD implant relative to the IPD tusk-shaped implant tool 23 and suitable for coupling the IPD implant to the IPD tusk-shaped implant tool 23.

Preferably, in accordance with an exemplary embodiment of the present invention, the trailing end 25 of the IPD tusk-shaped implant tool 23 may comprise one or more locating pins 26 each configured to be received by a corresponding female receivers (see numerical reference 20 in FIG. 6). Most preferably, in accordance with an exemplary embodiment of the present invention, the trailing end 25 of the IPD tusk-shaped implant tool 23 may comprise three locating pins 26 each configured to be received in to a corresponding female receivers (see numerical reference 20 in FIG. 6).

One of reasonable skill in the art understands that numerous means may be used to orientating the IPD implant relative to the IPD tusk-shaped implant tool 23 and suitable for coupling the IPD implant to the IPD tusk-shaped implant tool 23 and that all such means are contemplated and disclosed herein.

Additionally, in accordance with an exemplary embodiment of the present invention, the IPD tusk-shaped implant tool 23 may comprise a coating. In accordance with an exemplary embodiment of the present invention, the IPD tusk-shaped implant tool 23 may comprise a coating and/or be pretreated with any substance suitably configured to reduce trauma to the patient's tissue and/or spinous process, to maintain sterility of the device, to reduce inflammation, to protect against infection, to allow for imaging of the individual measurement sections, and/or to provide at least one of an analgesic, an anti-biotic, an anti-inflammatory, a polymeric release agent, an anti-proliferative agent, an anti-thrombotic agent, an anti-migratory agent, an antineoplastic agent, a fibrin growth factor, an anti-bacterial, an anti-mitotic agent, a vascular cell growth inhibitor, a cholesterol-lowering agent, a vasodilating agent, and/or a coagulant (anti-coagulant).

In accordance an exemplary embodiment of the present invention, the protective coating may comprise any biocompatible protective coating. For example, the biocompatible protective coating can include, but is not limited to a biocompatible polymer. The biocompatible polymer may include, but is not limited to, at least one of a polytetrafluoroethylene (PTFE), a polyurethane, a silicone, a polyurethane-urea, and a silicone-polyurethane polymer.

Currently, many biocompatible coatings are commercially available, but due to complex polymeric nature, these compounds are often referred to by their shorthand trade names, including, but not limited to GORE-TEX®, TEFLON®, Dacron®, Pellethane®, a Chronoflex®, a Hydrothane®, an Estane®, an Elast-Eon®, a Texin®, a Biomer®, a Surethane®, a Corethane®, a Carbothane®, a Technoflex®, a Tecothanem®, and a Biospan®.

One of reasonable skill in the art will understand that numerous coatings and pretreatments for medical tools, devices, and implants are known in the art and contemplated herein.

By way of non-limiting example, the curved, rigid, and cannulated body of the IPD tusk-shaped implant tool 23 may be made of steel coated in GORETEX® to reduce the coefficient of friction between the IPD tusk-shaped implant tool 23 and the patient's tissue. One of reasonable skill in the art understands that numerous material compositions may be used to produce and/or coat a curved, rigid, and cannulated body and that all such material compositions are contemplated and disclosed herein.

In accordance with an exemplary embodiment of the present invention, the curved, rigid, and cannulated body of the IPD tusk-shaped implant tool 23 may comprise a labeling material coupled to and/or incorporated inside the IPD tusk-shaped implant tool 23. Preferably, in accordance with an exemplary embodiment of the present invention, all or part of IPD tusk-shaped sizer 9 may comprise any labeling material useful for interacting with imaging energy including, but not limited to radiation energy (i.e. X-Rays), electromagnetic energy, sound energy, light energy, and/or any other energy used for therapeutic imaging.

The mechanism by which the label material interacts with the imaging energy is dependent upon the specific material and energy, as will be individually explained below. Additionally, the label material can be suitable metal alloys, suitable piezoelectric materials, and suitable radio-opaque materials. Optionally, in accordance with an exemplary embodiment, the label material may be biocompatible when coupled to and/or incorporated in the patch without an additional external coating.

Non-limiting examples of piezoelectric materials include crystals, including but not limited to at least one of a tourmaline crystal, a quartz crystal, a topaz crystal, a cane sugar crystal, a Rochelle salt crystal; quartz analogue crystals, including but not limited to berlinite ($AlPO_4$), gallium orthophosphate ($GaPO_4$), ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFeO_3$, $Na_xWO_3$, $Ba_2NaNb_5O_5$, $Pb_2KNb_5O_{15}$); and certain polymers, including but not limited to polyvinylidene fluoride, PVDF.

Non-limiting examples of radio-opaque, metal alloy materials include barium, iodine, bralium, bismuth, and/or tungsten.

As mentioned above, in accordance with an exemplary embodiment of the present invention, the energy used to image the labeling material coupled to and/or incorporated inside the IPD tusk-shaped implant tool 23 may be any imaging energy used for therapeutic imaging including, but not limited to radiation energy (i.e. X-Rays), electromagnetic energy, sound energy, and/or light energy. One of reasonable skill in the art will appreciate that there are numerous methods for therapeutic imaging, which utilize varying energies and energy waves to form images of patient tissue and implanted devices. As such, said person of reasonable skill will appreciate that such imaging means and energies are contemplated within the scope of this disclosure.

Most preferably, as illustrated in FIG. 7 and in accordance with an exemplary embodiment of the present invention, the IPD tusk-shaped implant tool 23 preferably comprises a diameter at the trailing end 25 equal to the leading edge 17 of the IPD implant 16 chosen by the physician.

Figure 8:
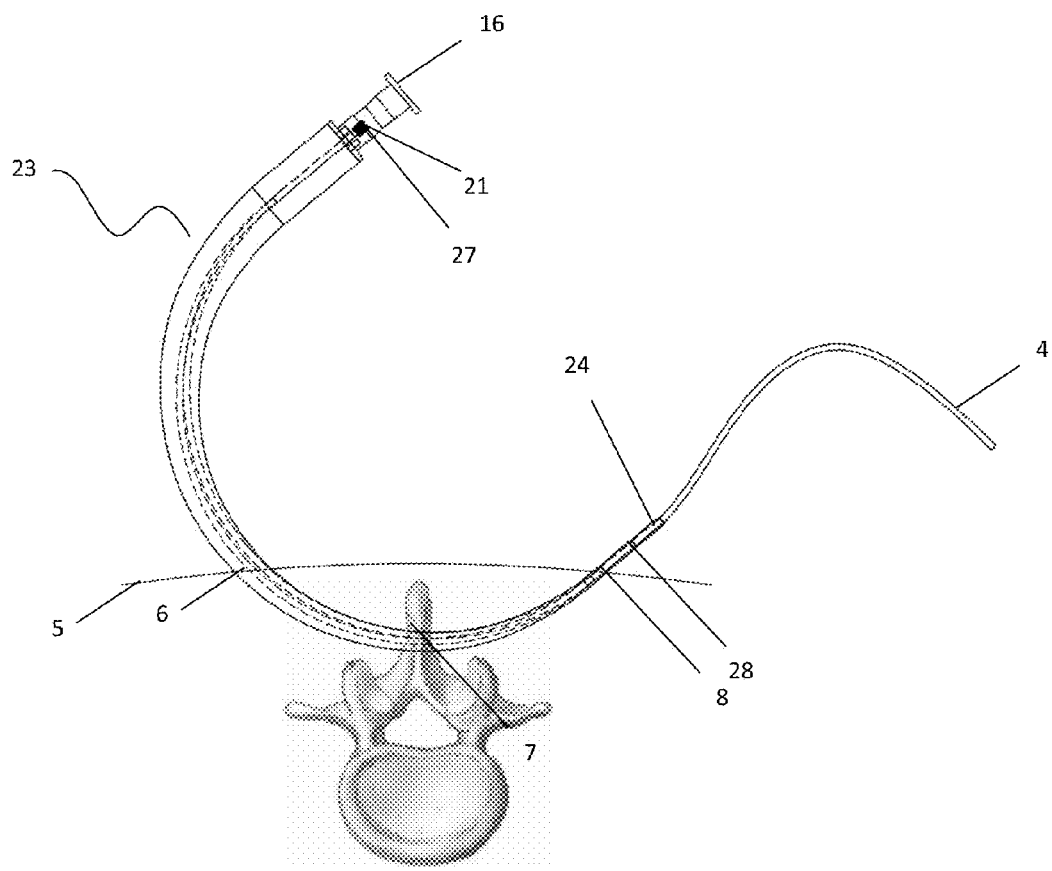
FIG. 8 illustrates a method for inserting an IPD implant in accordance with one exemplary embodiment of the present invention.

FIG. 8 illustrates a method for using an IPD tusk-shaped implant tool 23. Initially, in accordance with an exemplary embodiment of the present invention, IPD tusk-shaped implant tool 23 is placed around the guide wire 4 (guide wire 4 is passed through the IPD tusk-shaped implant tool 23), the threaded end 27 of guide wire 4 is then threaded in to the IPD implant 16 at threaded female channel 21, the guide wire 4 can then be pulled to locate the IPD implant 16 on one or more locating pins 26 of the IPD tusk-shaped implant tool 23. Once the IPD implant is orientated and coupled to the IPD tusk-shaped implant tool 23, in accordance with an exemplary embodiment of the present invention, set screw 28 can be tightened to secure and locate the IPD implant 16 relative to the IPD tusk-shaped implant tool 23. Now, in accordance with an exemplary embodiment of the present invention, IPD tusk-shaped implant tool 23 with secured IPD implant 16 may be percutaneously inserted in the skin on a patient's back 5 via a stab incision 6 (as discussed above).

Figure 9:
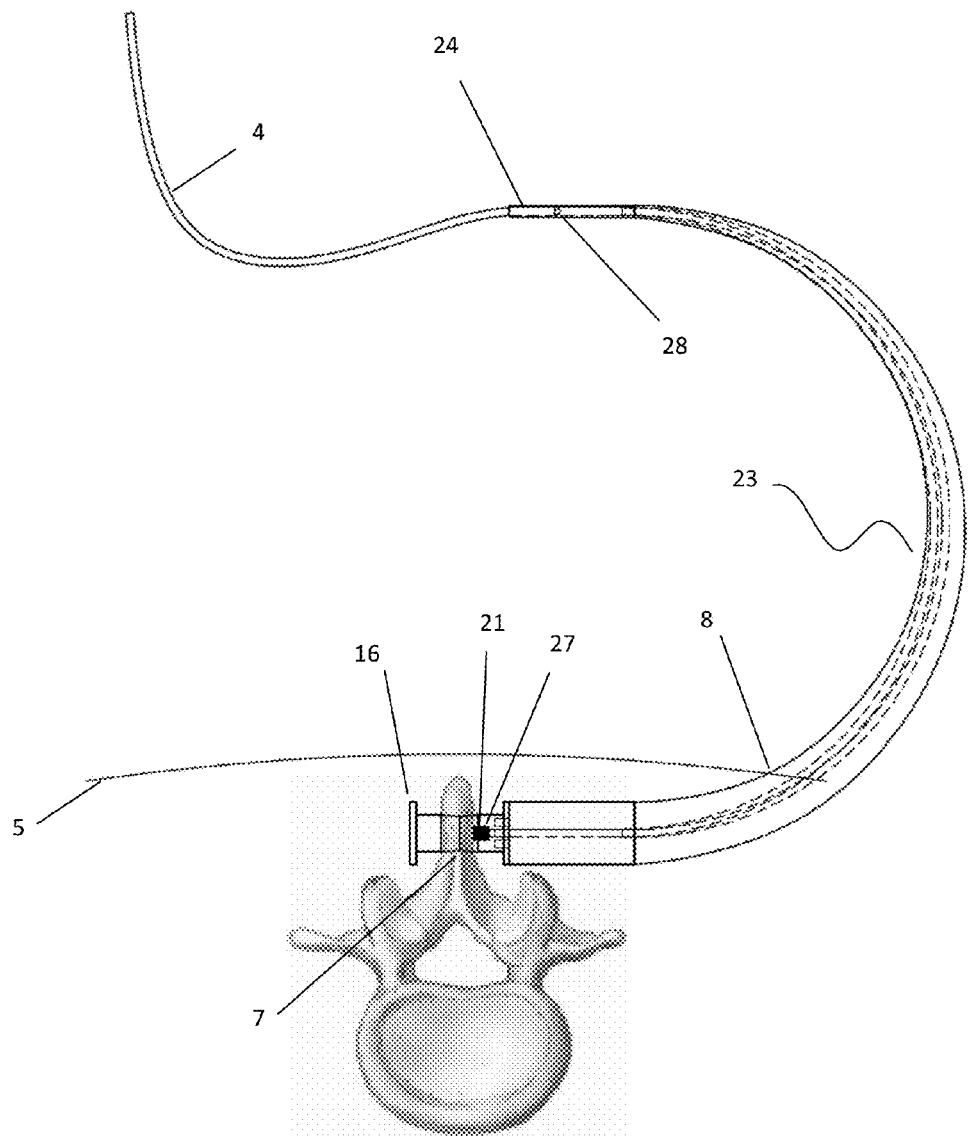
FIG. 9 illustrates a method for inserting an IPD implant in to a patient's spinous process in accordance with one exemplary embodiment of the present invention.

As illustrated in FIG. 9, in accordance with an exemplary embodiment of the invention, following the same path as the guide wire 4, the IPD tusk-shaped implant tool 23 may then be pushed on the trailing end 19 of the IPD implant 16 and/or pulled from the insertion end 24 by pulling on the guide wire 4 to be and rotated between the patient's spinous process 7. With reference to FIG. 8 and in accordance with an exemplary embodiment of the present invention, the IPD tusk-shaped implant tool 23 is pushed and/or pulled (moved or inserted) between the patient's spinous process 7 until the physician determines that the IPD implant 16 is secured within the patient's spinous process 7. One of reasonable skill in the art understands that determination of whether or not the IPD implant 16 is secure may depend on physician experience, imaging data (MRI or fluoroscopy), and/or physical data (pushing/pulling/moving to determine dilation and tissue rigidity).

In accordance with an exemplary embodiment of the present invention, the IPD tusk-shaped implant tool 23 is configured to protrude from the exit puncture wound 8 once the IPD implant enters the stab incision 6 in the patient's back 5.

Figure 10:
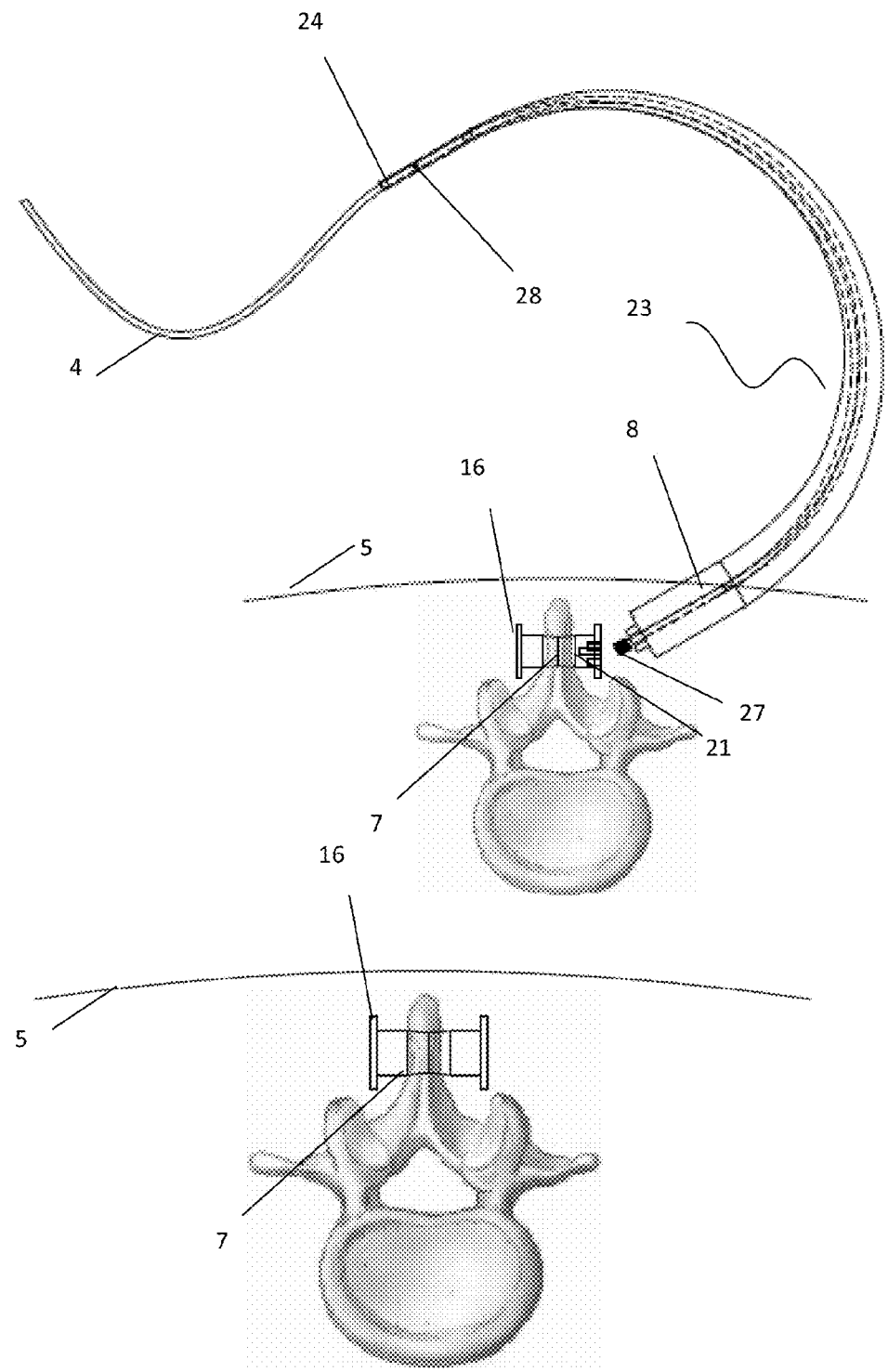
FIG. 10 illustrates a method for detaching an IPD implant and leaving the IPD implant between the patient's spinous process with in accordance with one exemplary embodiment of the present invention.

As illustrated in FIG. 10, in accordance with an exemplary embodiment of the invention, once the IPD implant 16 is secured in the patient's spinous process 7, guide wire 4 may be decoupled, most preferably by unthreading the threaded end 27 of guide wire 4 from the threaded female channel 21, from the IPD implant 16 and left in the patient's spinous process 7 to maintain proper dilation and to relieve the symptoms of spinal stenosis.

Methods for Use of Tusk-Shaped IPD Devices

In accordance with an exemplary embodiment of the present invention, the methods to percutaneously deliver and/or utilize the integrated IPD device(s), as described above, and to locate an IPD implant in a patient's spinous process vis-à-vis two simple stab incisions and preferably on an outpatient basis is taught herein.

Patient selection just like anything else in spinal surgery is important. Generally, the physician screens for elderly individuals that are less likely to tolerate laminectomy who have symptomatic spinal stenosis. Symptomatic means that the patients typically suffer from neurogenic claudication with pain into the legs in the upright and extended position and relief with sitting or in flexion.

Once the patient is selected, in accordance with an exemplary embodiment of the present invention, the appropriately sized IPD tusk kit comprising the components described herein is selected based on the depth from the skin to the intra-spinous process space. One of reasonable skill in the art of spinal stenosis surgical procedure will understand that a spinal stenosis tusk system or kit may comprise IPD tusk-shaped needles 1, IPD tusk-shaped sizers 9, and IPD tusk-shaped implant tool 23 in three general sizes—small, medium, and large (as described above).

Also, in accordance with an exemplary embodiment of the present invention, a large IPD tusk kit may have a linear height, h, of about 7 cm., a linear width, w, of 14 cm. (h=2×7 cm.=14 cm.), and an extra length, e, of 2 cm. This exemplary tusk would have a total height of 9 cm. and a total width of 14 cm.

Alternatively, one of reasonable skill in the art of spinal stenosis surgical procedure will understand that the largest size of the IPD tusk-shaped needle is constrained only by the proximity of the patient's internal organs and care should be taken in using the disclosed IPD tusk-shaped needle. This IPD tusk-shaped needle and surgical procedure may not be appropriate for a large person (i.e. where the distance from the patient's skin 5 to the spinous process 7 is greater than about 10 cm.). The risks associated with the procedure should be assessed by the treating physician for each specific patient.

Once the patient is screened, then the IPD tusk kit size may be determined. The procedure can start, preferably, under general or local anesthesia. In accordance with an exemplary embodiment of the present invention, the patient is placed in the Prone position for surgery, bi-planar fluoroscopy may be utilized for assuring proper placement, lumbar area is prepped and draped to assure sterility, the skin on the entry point 5 lateral to the spine is anesthetised with local anesthesia, and a stab incision is created here.

Preferably, in accordance with an exemplary embodiment of the present invention, the IPD tusk-shaped needle 1 is coupled to a guide wire 4 and percutaneously inserted in a patient's back via a stab incision 5 under fluoroscopic guidance between the spinous processes 7 of the affected level. The IPD tusk-shaped needle 1 is pushed (moved or inserted) between the patient's spinous process 7 and exits the patient's back through an exit puncture wound 8. In accordance with an exemplary embodiment of the present invention, the IPD tusk-shaped needle 1 is configure to stick out of both the stab incision entrance wound 5 and the exit puncture wound 8 (this area may also anesthetised with local anesthesia) simultaneously.

Secondly, in accordance with an exemplary embodiment of the present invention, the IPD tusk-shaped needle 1 is removed and the guide wire 4 is left in place. The guide wire will provide a guide for both the IPD tusk-shaped sizer 9 and the IPD tusk-shaped implant tool 23.

As described above, once the IPD tusk-shaped needle 1 is removed and the guide wire 4 is in place, the IPD tusk-shaped sizer 9 is placed around the guide wire 4 (guide wire 4 is passed through the IPD tusk-shaped sizer 9) and pushed/pulled/moved/inserted between the patient's spinous process 7 under fluoroscopy until the spinous process is sufficiently dilated and the IPD implant size 12 is determined for the patient. Preferably, in accordance with an exemplary embodiment of the present invention, the IPD tusk-shaped sizer 9 comprises a curved dilator suitable for percutaneous insertion between and sizing of a patient's spinous process. In accordance with an exemplary embodiment of the present invention, the IPD tusk-shaped sizer 9 is configured to protrude from both the stab incision entrance wound 5 and the exit puncture wound 8 simultaneously.

Most preferably, as previously described, in accordance with an exemplary embodiment of the present invention, the dilator portion of the IPD tusk-shaped sizer 9 comprises a measurement region 12, which gradually increases and is labeled for imaging. In accordance with an exemplary embodiment of the present invention, the IPD tusk-shaped sizer 9 is pushed and/or pulled (moved or inserted) between the patient's spinous process 7 and as fluoroscopic images the labeled segments in the measurement region 12 provide a visual reference and real-time measurement of the spinous process dilation. This measurement of the spinous process dilation is preferably then used to determine the size of the IPD implant to be used.

Once the patient's implant size is determined, the IPD tusk-shaped sizer 9 is either partially or fully removed. In one exemplary embodiment of the present invention, the measurement region 12 of the IPD tusk-shaped sizer 9 comprises detachably coupled measurement regions 14. In this exemplary embodiment, the IPD tusk-shaped sizer 9 is partially removed and all measurement regions 14 greater in diameter than the determined implant size for the patient are removed and replaced with an IPD implant 16 detachably coupled to the IPD tusk-shaped sizer 9 in any manner described herein.

In an alternative exemplary embodiment of the present invention as previously described, the IPD tusk-shaped sizer 9 is completely removed from the patient's back 5 and the guide wire 4 and an IPD tusk-shaped implant tool 23 is placed around the guide wire 4 (guide wire 4 is passed through the IPD tusk-shaped implant tool 23). In accordance with this exemplary embodiment, the IPD tusk-shaped implant tool 23 is pushed (moved or inserted) between a patient's spinous process 7 to dilate the patient's spinous process 7 until the detachable IPD implant 16 is securely positioned within the spinous process 7. Once the insertion portion of the IPD implant tool 23 exits the exit puncture wound 8, the IPD implant 16 is then pulled to securely place/implant in the patient's spinous process 7 with fluoroscopic (or with other known in the art imaging techniques) guidance.

Once, the IPD implant 16 is securely placed/implanted in the patient's spinous process 7, the IPD implant 16 is detached from the IPD tusk-shaped implant tool 23, the IPD tusk-shaped implant tool 23 (without the IPD implant) is removed from the patient's back 5, and the IPD implant 16 is left between the patient's spinous process. Finally, the two stab incisions (5 and 8) are then stitched closed.

Moreover, unless specifically noted, it is the Applicant's intent that the words and phrases in the specification and the claims be given the commonly accepted generic meaning or an ordinary and accustomed meaning used by those of reasonable skill in the applicable arts. In the instance where these meanings differ, the words and phrases in the specification and the claims should be given the broadest possible, generic meaning. If it is intended to limit or narrow these meanings, specific, descriptive adjectives will be used. Absent the use of these specific adjectives, the words and phrases in the specification and the claims should be given the broadest possible meaning. If any other special meaning is intended for any word or phrase, the specification will clearly state and define the special meaning.

As used herein, the terms "comprise", "comprises", "comprising", "having", "including", "includes", or any variation thereof, are intended to reference a non-exclusive inclusion, such that a process, method, article, composition or apparatus that comprises a list of elements does not include only those elements recited, but can also include other elements not expressly listed and equivalents inherently known or obvious to those of reasonable skill in the art. Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters or other operating requirements without departing from the scope of the instant invention and are intended to be included in this disclosure.

The use of the words "function", "means" or "step" in the specification or claims is not intended to invoke the provisions of 35 USC 112, Paragraph 6, to define the invention. To the contrary, if such provisions are intended to be invoked to define the invention, then the claims will specifically state the phrases "means for" or "step for" and a function, without recitation of such phrases of any material, structure, or at in support of the function. Contrastingly, the intention is NOT to invoke such provision when then claims cite a "means for" or a "step for" performing a function with recitation of any structure, material, or act in support of the function. If such provision is invoked to define the invention it is intended that the invention not be limited only to the specific structure, materials, or acts that are described in the preferred embodiments, but in addition to include any and all structures, materials, or acts that perform the claimed function, along with any and all known or later-developed equivalent materials, structures, or acts for performing the claimed function.

The invention claimed is:

1. A method comprising:
   passing a solid needle (1) coupled to a guide wire (4) between a patient's spinous processes (7);
   removing said needle (1) and threading said guide wire (4) between said spinous processes (7), wherein this step comprises creating an exit puncture wound (8) by pushing said needle (1) between a patient's spinous processes (7) until said needle (1) exits said patient's skin (5) and while leaving said guide wire (4) between said spinous processes (7);
   passing an inter-spinous process decompression (IPD) tusk-shaped sizer (9) guided by said guide wire (4) between said spinous processes (7);
   imaging said IPD tusk-shaped sizer (9) between said spinous processes (7) to determine a suitable IPD implant (16) size;
   removing said IPD tusk-shaped sizer (9) and leaving said guide wire (4) between said spinous processes (7);
   feeding said guide wire (4) through an IPD tusk-shaped implant tool (23) and coupling the guide wire (4) to an IPD implant (16);
   passing said IPD tusk-shaped implant tool (23) guided by said guide wire (4) and said IPD implant (16) coupled to the end of said guide wire (4) between said spinous processes (7);
   imaging said IPD implant tusk-shaped tool (23) between said spinous processes (7) to determine IPD implant (16) positioning;
   positioning and leaving said IPD implant (16) between said spinous processes (7); and removing said IPD implant tusk-shaped tool (23).

2. The method of claim 1, wherein the step of passing an IPD tusk-shaped sizer (9) guided by said guide wire (4) between said spinous processes (7) comprises passing said guide wire (4) through said IPD tusk-shaped sizer (9) and pushing said IPD tusk-shaped sizer (9) between said spinous processes (7) such that said IPD tusk-shaped sizer (9) follows the path of the guide wire (4).

3. The method of claim 2, wherein said step of passing said guide wire (4) through said IPD sizer (9) and pushing said IPD tusk-shaped sizer (9) between said spinous processes (7) such that said IPD tusk-shaped sizer (9) follows the path of the guide wire (4) further comprises securing and locking the guide wire (4) relative to said IPD tusk-shaped sizer (9).

4. The method of claim 3, wherein said step of securing and locking the guide wire (4) relative to said IPD tusk-shaped sizer (9) comprises tightening a set screw (15) in said insertion end (10) of said IPD tusk-shaped sizer (9) to secure said guide wire (4) relative to said IPD tusk-shaped sizer (9).

5. The method of claim 1, wherein the step of passing an IPD tusk-shaped implant tool (23) guided by said guide wire (4) and an IPD implant (16) coupled to the end of said guide wire (4) between said spinous processes (7) comprises passing said guide wire (4) through said IPD tusk-shaped implant tool (23), coupling said IPD implant (16) to the end of said guide wire (4), and pushing said IPD tusk-shaped implant tool (23) between said spinous processes (7) such that said IPD tusk-shaped implant tool (23) follows the path of the guide wire (4).

6. The method of claim 5, wherein said step of passing said guide wire (4) through said IPD tusk-shaped implant tool (23), coupling said IPD implant (16) to the end of said guide wire (4), and pushing said IPD tusk-shaped implant tool (23) between said spinous processes (7) such that said IPD tusk-shaped implant tool (23) follows the path of the guide wire (4) further comprises securing and locking the guide wire (4) relative to said IPD tusk-shaped implant tool (23).

7. The method of claim 6, wherein said step of securing and locking the guide wire (4) relative to said IPD tusk-shaped implant tool (23) comprises tightening a set screw (28) in said insertion end (24) of said IPD tusk-shaped implant tool (23) to secure said guide wire (4) relative to said IPD tusk-shaped implant tool (23).

8. The method of claim 1, wherein the step of positioning and leaving said IPD implant (16) between said spinous processes (7) comprises decoupling said IPD implant (16) from said guide wire (4) to leave said IPD implant (16) between said spinous processes (7).

9. The method of claim 1, said IPD tusk-shaped sizer (9) comprises a curved and cannulated body suitably configured to house a guide wire (4); an insertion end (10) at one end of said IPD tusk-shaped sizer (9) suitable for percutaneous insertion between the spinous processes (7); a trailing end (11) at the opposite end of said IPD tusk-shaped sizer (9) from said insertion end (10) suitable configured to move said IPD tusk-shaped sizer (9) between said spinous processes (7).

10. The method of claim 9, wherein said IPD tusk-shaped sizer (9) comprises a measurement region (12) located between said insertion end (10) and said trailing end (11).

11. The method of claim 10, wherein said measurement region (12) comprises labeled segments (14).

12. The method of claim 11, wherein said step of imaging said IPD tusk-shaped sizer (9) comprises imaging said labeled segments (12) of said measurement region (12).

13. The method of claim 9, wherein said measurement region (12) comprises a gradually increasing diameter with the smallest diameter closest to said insertion end (10) and the largest diameter closest to said trailing end (11).

14. The method of claim 1, wherein said IPD tusk-shaped implant tool (23) comprises a curved and cannulated body suitably configured to house a guide wire (4); an insertion end (24) at one end of said IPD tusk-shaped implant tool (23) suitable for percutaneous insertion between the spinous processes (7); a trailing end (25) at the opposite end of said IPD tusk-shaped implant tool (23) from said insertion end (24) configured to locate said IPD implant (16).

15. The method of claim 1, wherein said IPD implant comprises a cylindrical body (16) for implantation between the spinous processes (7) comprising a leading edge (17), a following edge (19), and a middle portion (18) between said leading edge (17) and said following edge (19), wherein said middle portion (18) is configured to dilate and maintain separation of said spinous processes (7).

16. A method comprising:
  selecting an inter-spinous process decompression (IPD) needle (1) coupled to a guide wire (4);
  creating a stab incision (6) by inserting said IPD needle (1) into a patient's skin (5);
  creating an exit puncture wound (8) by pushing said IPD needle (1) between a patient's spinous processes (7) until said IPD needle (1) exits said patient's skin (5);
  removing said IPD needle (1) from said patient's back, while leaving said guide wire (4) between said spinous processes (7);
  placing an IPD tusk-shaped sizer (9) around said guide wire (4);
  pushing said IPD tusk-shaped sizer (9) between said spinous processes (7);
  imaging said IPD tusk-shaped sizer (9) as said IPD tusk-shaped sizer (9) passes between said spinous processes (7) to determine a suitable IPD implant (16) size;
  removing said IPD tusk-shaped sizer (9) from said spinous processes (7);
  placing an IPD tusk-shaped implant tool (23) around said guide wire (4);
  coupling an IPD implant (16) to the end of said guide wire (4);
  locating said IPD implant (16) to the end of said IPD tusk-shaped implant tool (23);
  pushing said IPD tusk-shaped implant tool (23) between said spinous processes (7) until said IPD implant (16) said is securely positioned within said spinous processes (7);
  decoupling said IPD implant (16) from said guide wire (4); and
  removing said IPD tusk-shaped implant tool (23) from said patient's back by pulling said IPD tusk-shaped implant tool (23) from said exit puncture wound (8).

* * * * *